(12) United States Patent
Kim et al.

(10) Patent No.: US 10,227,437 B2
(45) Date of Patent: *Mar. 12, 2019

(54) BLOCK COPOLYMER

(71) Applicant: LG Chem, Ltd., Seoul (KR)

(72) Inventors: Jung Keun Kim, Daejeon (KR); Je Gwon Lee, Daejeon (KR); No Jin Park, Daejeon (KR); Sung Soo Yoon, Daejeon (KR)

(73) Assignee: LG Chem, Ltd. (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/102,089

(22) PCT Filed: Dec. 8, 2014

(86) PCT No.: PCT/KR2014/012027
§ 371 (c)(1),
(2) Date: Jun. 6, 2016

(87) PCT Pub. No.: WO2015/084124
PCT Pub. Date: Jun. 11, 2015

(65) Prior Publication Data
US 2016/0311958 A1    Oct. 27, 2016

(30) Foreign Application Priority Data

| Dec. 6, 2013 | (KR) | 10-2013-0151865 |
| Dec. 6, 2013 | (KR) | 10-2013-0151866 |
| Dec. 6, 2013 | (KR) | 10-2013-0151867 |
| Dec. 20, 2013 | (KR) | 10-2013-0159994 |
| Sep. 30, 2014 | (KR) | 10-2014-0131964 |
| Dec. 8, 2014 | (KR) | 10-2014-0175406 |

(51) Int. Cl.
| C08F 293/00 | (2006.01) |
| C08J 7/12 | (2006.01) |
| C08J 7/14 | (2006.01) |
| C07F 7/18 | (2006.01) |
| C07C 43/215 | (2006.01) |
| C07C 43/225 | (2006.01) |
| C07C 217/84 | (2006.01) |
| C07D 209/48 | (2006.01) |
| C08F 12/20 | (2006.01) |
| C08F 12/22 | (2006.01) |
| C08F 12/26 | (2006.01) |
| C08F 12/32 | (2006.01) |
| C08F 212/14 | (2006.01) |
| C08F 220/10 | (2006.01) |
| C08F 220/30 | (2006.01) |
| C08J 5/18 | (2006.01) |
| G03F 7/00 | (2006.01) |
| C07C 35/48 | (2006.01) |
| C09D 153/00 | (2006.01) |
| G03F 7/038 | (2006.01) |
| G03F 7/039 | (2006.01) |
| G03F 7/16 | (2006.01) |
| B81C 1/00 | (2006.01) |
| B82Y 40/00 | (2011.01) |

(52) U.S. Cl.
CPC .......... *C08F 293/005* (2013.01); *C07C 35/48* (2013.01); *C07C 43/215* (2013.01); *C07C 43/225* (2013.01); *C07C 217/84* (2013.01); *C07D 209/48* (2013.01); *C07F 7/1804* (2013.01); *C08F 12/20* (2013.01); *C08F 12/22* (2013.01); *C08F 12/26* (2013.01); *C08F 12/32* (2013.01); *C08F 212/14* (2013.01); *C08F 220/10* (2013.01); *C08F 220/30* (2013.01); *C08J 5/18* (2013.01); *C08J 7/123* (2013.01); *C08J 7/14* (2013.01); *C09D 153/00* (2013.01); *G03F 7/0002* (2013.01); *G03F 7/038* (2013.01); *G03F 7/039* (2013.01); *G03F 7/162* (2013.01); *B81C 1/00428* (2013.01); *B81C 1/00531* (2013.01); *B81C 2201/0149* (2013.01); *B82Y 40/00* (2013.01); *C07C 2601/16* (2017.05); *C08F 2438/03* (2013.01); *C08J 2353/00* (2013.01)

(58) Field of Classification Search
None
See application file for complete search history.

(56) References Cited

U.S. PATENT DOCUMENTS

| 3,976,672 A | 8/1976 | Strunk et al. |
| 5,115,056 A | 5/1992 | Mueller et al. |
| 5,202,402 A | 4/1993 | Funaki et al. |
| 5,234,604 A | 8/1993 | Liao et al. |

(Continued)

FOREIGN PATENT DOCUMENTS

| CN | 1333790 A | 1/2002 |
| CN | 1337974 A | 2/2002 |

(Continued)

OTHER PUBLICATIONS

Machine translation of KR100622353 downloaded Mar. 18, 2017.*

(Continued)

*Primary Examiner* — Irina S Zemel
*Assistant Examiner* — Jeffrey S Lenihan
(74) *Attorney, Agent, or Firm* — Lerner, David, Littenberg, Krumholz & Mentlik, LLP

(57) ABSTRACT

The present application provides the block copolymers and their application. The block copolymer has an excellent self assembling property and phase separation and various required functions can be freely applied thereto as necessary.

21 Claims, 11 Drawing Sheets

(56) References Cited

U.S. PATENT DOCUMENTS

| | | |
|---|---|---|
| 5,391,626 A | 2/1995 | Machida et al. |
| 5,418,290 A | 5/1995 | Machida et al. |
| 5,554,695 A | 9/1996 | Machida et al. |
| 5,728,431 A | 3/1998 | Bergbreiter et al. |
| 6,314,225 B1 | 11/2001 | Wang |
| 6,531,547 B1 | 3/2003 | Visger et al. |
| 6,546,282 B1 | 4/2003 | Inoue et al. |
| 6,953,649 B2 | 10/2005 | Prat et al. |
| 7,538,159 B2 | 5/2009 | Wang et al. |
| 8,163,189 B2 | 4/2012 | Iyoda et al. |
| 8,211,737 B2 | 7/2012 | Russell et al. |
| 8,791,042 B2 | 7/2014 | Ronan et al. |
| 9,495,991 B2 | 11/2016 | Han et al. |
| 2003/0143343 A1 | 7/2003 | Kawabata et al. |
| 2004/0049836 A1 | 3/2004 | Ashraf et al. |
| 2004/0110856 A1 | 6/2004 | Young et al. |
| 2004/0143032 A1 | 7/2004 | Auschra et al. |
| 2004/0242787 A1* | 12/2004 | Chun .................... C08F 297/04 525/242 |
| 2006/0166033 A1 | 7/2006 | Poetsch et al. |
| 2007/0142559 A1 | 6/2007 | Wang et al. |
| 2007/0166648 A1 | 7/2007 | Ponoth et al. |
| 2007/0219338 A1 | 9/2007 | Takeda et al. |
| 2008/0105854 A1 | 5/2008 | Huh et al. |
| 2008/0193658 A1 | 8/2008 | Millward |
| 2008/0286333 A1 | 11/2008 | Kangas et al. |
| 2008/0311402 A1 | 12/2008 | Jung et al. |
| 2009/0114108 A1 | 5/2009 | Oya et al. |
| 2009/0240001 A1 | 9/2009 | Regner |
| 2009/0253867 A1 | 10/2009 | Takahashi et al. |
| 2009/0306295 A1 | 12/2009 | Mays et al. |
| 2010/0086801 A1 | 4/2010 | Russell et al. |
| 2010/0098876 A1 | 4/2010 | Hanson |
| 2010/0102415 A1 | 4/2010 | Millward et al. |
| 2010/0120985 A1 | 5/2010 | Konishi et al. |
| 2010/0155988 A1 | 6/2010 | Keil et al. |
| 2010/0206057 A1 | 8/2010 | Batchelder et al. |
| 2010/0210742 A1 | 8/2010 | Iyoda et al. |
| 2010/0216312 A1 | 8/2010 | Yamamoto et al. |
| 2010/0266957 A1 | 10/2010 | Harada et al. |
| 2010/0285276 A1 | 11/2010 | Kim et al. |
| 2010/0286351 A1 | 11/2010 | Yoshida et al. |
| 2010/0305230 A1 | 12/2010 | Li et al. |
| 2011/0186544 A1 | 8/2011 | Endou et al. |
| 2011/0253946 A1 | 10/2011 | Huh et al. |
| 2011/0294070 A1 | 12/2011 | Hatakeyama et al. |
| 2012/0052446 A1 | 3/2012 | Jaycox et al. |
| 2012/0116024 A1 | 5/2012 | Iyoda et al. |
| 2012/0214094 A1 | 8/2012 | Mikoshiba et al. |
| 2013/0078576 A1 | 3/2013 | Wu et al. |
| 2013/0183828 A1 | 7/2013 | Nakamura et al. |
| 2013/0189504 A1 | 7/2013 | Nealey et al. |
| 2013/0209693 A1 | 8/2013 | Vogel et al. |
| 2013/0209755 A1 | 8/2013 | Hustad et al. |
| 2013/0248488 A1 | 9/2013 | Han et al. |
| 2013/0284698 A1 | 10/2013 | Ogihara |
| 2013/0306594 A1 | 11/2013 | Hustad et al. |
| 2014/0011916 A1 | 1/2014 | Lee et al. |
| 2014/0127456 A1 | 5/2014 | Regner |
| 2014/0141375 A1 | 5/2014 | Cho et al. |
| 2014/0238954 A1 | 8/2014 | Matsumiya et al. |
| 2014/0370442 A1 | 12/2014 | Ober et al. |
| 2015/0064630 A1 | 3/2015 | Wuister et al. |
| 2015/0085042 A1 | 3/2015 | Keoshkerian et al. |
| 2015/0197663 A1 | 7/2015 | Mizutani et al. |
| 2015/0228298 A1 | 8/2015 | Han et al. |
| 2016/0204653 A1 | 7/2016 | Lee |
| 2016/0257838 A1 | 9/2016 | Senzaki et al. |
| 2016/0280823 A1 | 9/2016 | Kim et al. |
| 2016/0280831 A1 | 9/2016 | Park et al. |
| 2016/0280832 A1 | 9/2016 | Kim et al. |
| 2016/0280833 A1 | 9/2016 | Lee et al. |
| 2016/0280834 A1 | 9/2016 | Kim et al. |
| 2016/0280835 A1 | 9/2016 | Lee et al. |
| 2016/0304653 A1 | 10/2016 | Kim et al. |
| 2016/0304654 A1 | 10/2016 | Lee et al. |
| 2016/0304655 A1 | 10/2016 | Lee et al. |
| 2016/0311958 A1 | 10/2016 | Kim et al. |
| 2016/0311959 A1 | 10/2016 | Lee et al. |
| 2016/0311960 A1 | 10/2016 | Lee et al. |
| 2016/0333221 A1 | 11/2016 | Mumtaz et al. |
| 2017/0008992 A1 | 1/2017 | Lee et al. |
| 2017/0058071 A1 | 3/2017 | Lee et al. |
| 2017/0210938 A1 | 7/2017 | Ku et al. |
| 2017/0219922 A1 | 8/2017 | Ku et al. |
| 2017/0226235 A1 | 8/2017 | Park et al. |
| 2017/0226258 A1 | 8/2017 | Lee et al. |
| 2017/0226260 A1 | 8/2017 | Lee et al. |
| 2017/0226261 A1 | 8/2017 | Lee et al. |
| 2017/0247492 A1 | 8/2017 | Choi et al. |
| 2017/0306074 A1 | 10/2017 | Lee et al. |
| 2017/0313869 A1 | 11/2017 | Lee et al. |
| 2018/0170023 A1 | 6/2018 | Park et al. |

FOREIGN PATENT DOCUMENTS

| | | |
|---|---|---|
| CN | 101215362 A | 7/2008 |
| CN | 101443371 A | 5/2009 |
| CN | 101492520 A | 7/2009 |
| CN | 101578232 A | 11/2009 |
| CN | 101688047 A | 3/2010 |
| CN | 101799626 A | 8/2010 |
| CN | 101977839 A | 2/2011 |
| CN | 102172491 A | 9/2011 |
| CN | 102439076 A | 5/2012 |
| CN | 102967918 A | 3/2013 |
| CN | 103025827 A | 4/2013 |
| CN | 103180783 A | 6/2013 |
| CN | 103289285 A | 9/2013 |
| CN | 103562245 A | 2/2014 |
| CN | 105899556 A | 8/2016 |
| CN | 105899557 A | 8/2016 |
| CN | 105899559 A | 8/2016 |
| CN | 105899560 A | 8/2016 |
| CN | 105934454 A | 9/2016 |
| CN | 105934456 A | 9/2016 |
| CN | 105960422 A | 9/2016 |
| CN | 105980342 A | 9/2016 |
| CN | 106459326 A | 2/2017 |
| EP | 1141056 B1 | 8/2010 |
| EP | 2781550 A1 | 9/2014 |
| EP | 3078654 A1 | 10/2016 |
| EP | 3078691 B1 | 10/2016 |
| EP | 3078692 A1 | 10/2016 |
| EP | 3078694 A1 | 10/2016 |
| EP | 3203497 A1 | 8/2017 |
| EP | 3214102 A1 | 9/2017 |
| EP | 3225641 A1 | 10/2017 |
| GB | 898065 A | 6/1962 |
| JP | 01260360 A | 10/1989 |
| JP | H01-260360 A | 10/1989 |
| JP | H5320281 A | 12/1993 |
| JP | H0665333 A | 3/1994 |
| JP | H10237143 A | 9/1998 |
| JP | H10245427 A | 9/1998 |
| JP | H1143523 A | 2/1999 |
| JP | 2000053734 A | 2/2000 |
| JP | 2000281737 A | 10/2000 |
| JP | 2000285751 A | 10/2000 |
| JP | 3121116 B2 | 12/2000 |
| JP | 2001513125 A | 8/2001 |
| JP | 2001294617 A | 10/2001 |
| JP | 2002145973 A | 5/2002 |
| JP | 2003536105 A | 12/2003 |
| JP | 2004026688 A | 1/2004 |
| JP | 2004323773 A | 11/2004 |
| JP | 2005015508 A | 1/2005 |
| JP | 2005097442 A | 4/2005 |
| JP | 2005148205 A | 6/2005 |
| JP | 2005530030 A | 10/2005 |
| JP | 2005531618 A | 10/2005 |
| JP | 2007070453 A | 3/2007 |
| JP | 2007077292 A | 3/2007 |
| JP | 2007246600 A | 9/2007 |

(56) References Cited

FOREIGN PATENT DOCUMENTS

| | | |
|---|---|---|
| JP | 2009057519 A | 3/2009 |
| JP | 200986354 A | 4/2009 |
| JP | 2009203439 A | 9/2009 |
| JP | 2010507803 A | 3/2010 |
| JP | 2010115832 A | 5/2010 |
| JP | 2010145158 A | 7/2010 |
| JP | 2010202723 A | 9/2010 |
| JP | 2010275349 A | 12/2010 |
| JP | 4625901 B2 | 2/2011 |
| JP | 2012001787 A | 1/2012 |
| JP | 2012012577 A | 1/2012 |
| JP | 2012093699 A | 5/2012 |
| JP | 2012174984 A | 9/2012 |
| JP | 201368882 A | 4/2013 |
| JP | 2013512323 A | 4/2013 |
| JP | 2013514449 A | 4/2013 |
| JP | 2013121430 A | 6/2013 |
| JP | 2013219334 A | 10/2013 |
| JP | 2013232501 A | 11/2013 |
| JP | 201412807 A | 1/2014 |
| JP | 2014070154 A | 4/2014 |
| JP | 2014102503 A | 6/2014 |
| JP | 2015000896 A | 1/2015 |
| JP | 2016539239 A | 12/2016 |
| JP | 2016540863 A | 12/2016 |
| JP | 2017502116 A | 1/2017 |
| JP | 2017505356 A | 2/2017 |
| JP | 2017530236 A | 10/2017 |
| JP | 2017530238 A | 10/2017 |
| JP | 2017533302 A | 11/2017 |
| KR | 20010101356 | 11/2001 |
| KR | 100622353 B1 | 9/2006 |
| KR | 20090015742 A | 2/2009 |
| KR | 100935863 B1 | 1/2010 |
| KR | 20100033962 A | 3/2010 |
| KR | 20100070380 A | 6/2010 |
| KR | 20100123920 A | 11/2010 |
| KR | 20110018678 A | 2/2011 |
| KR | 20110086834 A | 8/2011 |
| KR | 20110097707 A | 8/2011 |
| KR | 20110102998 A | 9/2011 |
| KR | 20110112501 A | 10/2011 |
| KR | 101102680 B1 | 1/2012 |
| KR | 20120119998 A | 11/2012 |
| KR | 20130094264 A | 8/2013 |
| KR | 20130113596 A | 10/2013 |
| KR | 20130128346 A | 11/2013 |
| KR | 20140063790 A | 5/2014 |
| KR | 20150066488 A | 6/2015 |
| KR | 20150067065 A | 6/2015 |
| KR | 20150067069 A | 6/2015 |
| KR | 20150067070 A | 6/2015 |
| KR | 20160038705 A | 4/2016 |
| TW | 201323461 A | 6/2013 |
| TW | 201428046 A | 7/2014 |
| TW | 201536823 A | 10/2015 |
| TW | 201538548 A | 10/2015 |
| WO | 9837136 A1 | 8/1998 |
| WO | 2007055371 A1 | 5/2007 |
| WO | 2012144735 A2 | 10/2012 |
| WO | 2013069544 A1 | 5/2013 |
| WO | 2013120051 A1 | 8/2013 |
| WO | 2013158527 A1 | 10/2013 |
| WO | 2014050905 A1 | 4/2014 |
| WO | 2014090178 A1 | 6/2014 |
| WO | 2014124795 A1 | 8/2014 |
| WO | 2015084121 A1 | 6/2015 |
| WO | 2015084122 A1 | 6/2015 |
| WO | 2015084123 A1 | 6/2015 |
| WO | 2015084124 A1 | 6/2015 |
| WO | 2015084125 A1 | 6/2015 |
| WO | 2015084126 A1 | 6/2015 |
| WO | 2015084127 A1 | 6/2015 |
| WO | 2015087005 A1 | 6/2015 |
| WO | 2016052994 A1 | 4/2016 |
| WO | 2016052999 A1 | 4/2016 |
| WO | 2016053005 A1 | 4/2016 |
| WO | 2016053007 A1 | 4/2016 |
| WO | 2016053011 A1 | 4/2016 |

OTHER PUBLICATIONS

International Search Report from PCT/KR2014/012023, dated Mar. 10, 2015.
IPO Search Report from Taiwan Application No. 103142955, dated Jan. 15, 2016.
International Search Report from PCT/KR2014/012024, dated Mar. 17, 2015.
IPO Search Report from Taiwan Application No. 103142805, dated Dec. 11, 2015.
International Search Report from PCT/KR2014/012025, dated Mar. 17, 2015.
IPO Search Report from Taiwan Application No. 103142784, dated Jan. 27, 2016.
International Search Report from PCT/KR2014/012026, dated Mar. 17, 2015.
International Search Report from PCT/KR2014/012027, dated Mar. 17, 2015.
IPO Search Report from Tawain Application No. 103142782, dated Dec. 11, 2015.
International Search Report from PCT/KR2014/012028, dated Mar. 17, 2015.
IPO Search Report from Taiwan Application No. 103142798, dated Dec. 16, 2015.
International Search Report from PCT/KR2014/012029, dated Mar. 17, 2015.
IPO Search Report from Taiwan Application No. 103142780, dated Dec. 15, 2015.
International Search Report from PCT/KR2014/012030, dated Mar. 17, 2015.
IPO Search Report from Taiwan Application No. 103142790, dated Dec. 15, 2015.
International Search Report from PCT/KR2014/012031, dated Feb. 12, 2015.
IPO Search Report from Taiwan Application No. 103142956 dated Jan. 20, 2016.
International Search Report from PCT/KR2014/012032, dated Feb. 12, 2015.
IPO Search Report from Taiwan Application No. 103142777, dated Dec. 15, 2015.
International Search Report from PCT/KR2014/012033, dated Feb. 12, 2015.
IPO Search Report from Taiwan Application No. 103142963, dated Dec. 10, 2015.
International Search Report from PCT/KR2014/012034, dated Feb. 12, 2015.
IPO Search Report from Taiwan Application No. 103142745, dated Dec. 14, 2015.
International Search Report from PCT/KR2014/012035, dated Feb. 12, 2015.
Akiba, Isamu, et al., "Self-Assembly of Amphiphilic Block Copolymers Containing Poly(n-octadecyl acrylate) Block in Aqueous Solution." IOP Conference Series: Materials Science and Engineering, 2010, vol. 14, No. 1, pp. 1-8.
IPO Search Report from Taiwan Application No. 103142794, dated Dec. 15, 2015.
IPO Search Report from Taiwan Application No. 103142786, dated Jan. 11, 2016.
International Search Report from PCT/KR2014/012036, dated Mar. 17, 2015.
CN Search Report for Application No. 201480071920.0 dated Aug. 2, 2017.
CN Search Report for Application No. CN201480072884.X dated Aug. 3, 2017.
CN Search Report for Application No. CN2014800740447 dated Aug. 1, 2017.

(56) References Cited

OTHER PUBLICATIONS

Extended European Search Report for Application No. EP14867273 dated Aug. 10, 2017.
Mariana Beija et al: "Fluorescence Anisotropy of Hydrophobic Probes in poly(N-decylacrylamide) block-poly( N, N-diethylacrylamide) Block Copolymer Aqueous Solutions: Evidence of Premicellar Aggregates" Journal of Physical Chemistry Part B: Condensed Matter, Materials, Surfaces, Interfaces & Biophysical, vol. 114, No. 31, Aug. 12, 2010 (Aug. 12, 2010), 9977-9986, XP055394763, US ISSN: 1520-6106, DOI: 10.1021/jp101613y * abstract * * Scheme 1, PDcA11-block-PDEA295; p. 9978 *.
Hua et al. Temperature-induced phase-transitions of methoxyoligo(oxyethylene) styrene-based block copolymers in aqueous solution, Soft Matter, 2013, 9, 8897.
International Search Report from PCT/KR2015/010313, dated Nov. 23, 2015.
International Search Report from PCT/KR2015/010320, dated Jan. 13, 2016.
International Search Report from PCT/KR2015/010322, dated Jan. 13, 2016.
International Search Report from PCT/KR2015/010323, dated Jan. 13, 2016.
International Search Report from PCT/KR2015/010327, dated Jan. 12, 2016.
International Search Report from PCT/KR2015/010330 dated Jan. 11, 2016.
International Search Report from PCT/KR2015/010332 dated Jan. 13, 2016.
International Search Report from PCT/KR2015/010334, dated Jan. 13, 2016.
International Search Report from PCT/KR2015/010335 dated Jan. 13, 2016.
International Search Report from PCT/KR2015/010338 dated Jan. 14, 2016.
IPO Search Report from Taiwan Application No. 104132186, dated Aug. 18, 2016.
Khazimullis et al. "Gel formation in a mixture of a block copolymer and a nematic liquid crystal", Physical Review E 84, 021710 (2011).
Park et al., "Block Copolymer Lithography: Periodic Arrays of ~10 11 Holes in 1 Square Centimeter", Science 276, p. 1401-1404, May 30, 1997.
Tenneti et al. "Competition between liquid crystallinity and block copolymer self-assembly in core-shell rod-coil block copolymers", Soft Matter, 2008, 4, 458-461 (2008).
Tenneti et al. Hierarchical Nanostructures of Mesogen Jacketed Bent-Core Liquid Crystalline Block Copolymers, Proceedings Published 2007 by the American Chemical Society.
Database CA [Online] Chemical Abstracts Service Ohio US; Zou, Yue: "Fluorosurfactant capable of preventing unevenness in photoresist coating and its preparation by anionic polymerization", XP002771143 retrieved from STN Database accession No. 2011:1148166 * abstract * & CN 102 172 491 A (Jiangsu Johnny Material Technology Co Ltd) Sep. 7, 2011 (Sep. 7, 2011) Columbus, No. 2011:1148166.
European Search Report for Application No. EP14867501 dated Jul. 14, 2017.
Kago K et al: "X-ray reflectivity of polymer assembly at air-water interface" Supramolecular Science Butterworth-Heinemann Oxford GB vol. 5 No. 3-4, Jul. 1, 1998 (Jul. 1, 1998)pp. 349-355 XP027388373 ISSN: 0968-5677 [retrieved on Jul. 1, 1998]* abstract *.
Lutz Funk et al: "Novel Amphiphilic Styrene-Based Block Copolymers for Induced Surface Reconstruction". Macromolecular Chemistry and Physics., vol. 209, No. 1, Jan. 4, 2008 (Jan. 4, 2008), XP055382259 DE ISSN: 1022-1352 DOI: 10.1002/macp. 200700312 * scheme 1, monomers M1, M4 table 2*.
Mori H et al: "Synthesis and Surface Characterization of Hydrophilic-Hydrophobic Block Copolymers Containing Poly(2, 3-Dihydroxypropyl Methacrylate)" Macromolecules American Chemical Society US vol. 27 No. 15 Jul. 18, 1994 (Jul. 18, 1994) pp. 4093-4100 XP000456650 ISSN: 0024-9297 D01: 10.1021/MA00093A010 * abstract *.
Riedel et al., Synthesis, post-modification and self-assembled thin films of pentafluorostyrene containing block copolymers, European Polymer Journal 47 (2011) 675-684.
Yoshida, E. et al. Polymer Journal vol. 31 (5) pp. 429-434 (1999).
Chinese Search Report for Application No. 201480072759.9 dated Jan. 24, 2018.
Palacios et al., Constructing Robust and Functional Micropatterns on Polystyrene Surfaces by Using Deep UV Irradiation, American Chemical Society, Langmuir, 29(8) pp. 2756-2763, Feb. 2013.
Chinese Search Report for Application No. 2014800727599 dated Jan. 8, 2018.
Chinese Search Report for Application No. 2014800741401 dated Mar. 9, 2018.
Chinese Search Report for Application No. 201480074156.2 dated Apr. 3, 2018.
Supplementary European Search Report for EP15847157 dated Mar. 21, 2018.
Anonymous., "Solid surface energy data (SFE) for common polymers", surface-tension.de, Feb. 2017, Retreived rom the Internet: URL:http://www.surface-tension.de/solid-surface-energy.htm, XP002775246.
Cummins et al., "Solvothermal Vapor Annealing of Lamellar Poly-(styrene)-block-poly(D,L-lactide) Block Copolymer Thin Films for Directed Self-Assembly Application", ACS Applied Materials & Interfaces, Mar. 2016, vol. 8, No. 12, pp. 8295-8304, XP055419698.
Extended European Search Report for Application No. EP14867808.9 dated Nov. 10, 2017.
Extended European Search Report for Application No. EP14868022.6 dated Nov. 6, 2017.
Extended European Search Report for Application No. EP14868320.4 dated Nov. 20, 2017.
Extended European Search Report for Application No. EP14868480.6 dated Nov. 2, 2017.
Hvilsted et al., "Novel Fluorinated Polymer Materials Based on 2,3,5,6-Tetrafluoro-4-methoxyystyrene" In: "Advances in Controlled/ Living Radical Polymerization", American Chemical Society, Jun. 26, 2003, vol. 854, pp. 236-249, XP055421064.
Mahajan et al., "Synthesis and Characterization of Amphiphilic Poly(ethylene oxide)-block-poly(hexylmethacrylate Copolymers", Macromolecular Chemistry and Physics, Wiley-Vch Verlag, Weinheim, DE, Jan. 2003, vol. 204, pp. 1047-1055, XP003030406.
Pochan et al., "Morphologies of microphase-seperated conformationally asymmetric diblock copolymers", Journal of Polymer Science Part B: Polymer Physics, Nov. 2017, vol. 35, No. 16, pp. 2629-2643, XP055417266.
Zhuang et al., "Synthesis of A-B type block copolymers using 1-phenylethyl dithiobenzoate as Reversible Addition-Fragmentation Chain Transfer agent", Database CA [online], Chemical Abstracts Service, Columbus, OH, XP002775247.
Beng H. Tan et al., "Synthesis and Self-Assembly of pH-Responsive Amphiphilic Poly (dimethylaminoethylmethacrylate)-block-Poly(pentafluorostyrene) Block Copolymer in Aqueous Solution", Macromolecular Rapid Communications, Jun. 17, 2009, vol. 30 (12), pp. 1002-1008.
C.M. Bates et al., "Polymeric Cross-Linked Surface Treatments for Controlling Block Copolymer Orientation in Thin Films", Langmuir Article, American Chemical Society, Jan. 7, 2011, vol. 27, No. 5, pp. 1-7.
Chinese Search Report for CN Application No. 201480071920.0, dated May 4, 2018, completed Apr. 25, 2018.
Chinese Search Report for CN Application No. 201480072800.2, dated Apr. 10, 2018, completed Mar. 27, 2018.
Chinese Search Report for CN Application No. 2014800740447 dated Jun. 7, 2018, completed May 30, 2018.
Chinese Search Report for CN Application No. 201480074045.1, dated Apr. 11, 2018, completed Mar. 29, 2018.
Extended European Seach Report including Written Opinion for EP Application No. 15847574.9, dated May 3, 2018.
Extended European Search Report including Written Opinion for Application No. EP15845665.7 dated Jun. 27, 2018.

(56) References Cited

OTHER PUBLICATIONS

Extended European Search Report including Written Opinion for EP Application No. 15845928.9, dated May 2, 2018.
Extended European Search Report including Written Opinion for EP Application No. 15847598.8, dated May 11, 2018.
Extended European Search Report including Written Opinion for EP15845720.0 dated May 4, 2018.
Extended European Search Report with Written Opinion for EP158468322 dated May 3, 2018.
Frank S. Bates et al., "Block Copolymer Thermodyanmics: Theory and Experiment", Annu. Rev. Phys. Chem., Oct. 1990, vol. 41 (1), pp. 525-557.
Funk, L. et al., "Novel Amphiphilic Styrene-Based Block Copolymers for Induced Surface Reconstruction," Macromolecular Chemistry and Physics, vol. 209, No. 1, Jan. 4, 2008, pp. 52-63, XP055382259.
G.R. Strobl, "The Physics of Polymers: Concepts for Understanding Their Structures and Behavior", Springer (Abstract Only).
Haeng-Dong Koh et al., "Location-controlled parallel and vertical orientation by dewetting-induced block copolymer directed self-assembly," Journal of Materials Chemistry C: Materials for Optical and Electronic Devices, vol. 1, No. 25, Jan. 1, 2013, pp. 4020-4024 XP055469744.
Katja Nilles et al., "RAFT Polymerization of Activated 4-Vinylbenzoates"., Journal of Polymer Science: Part A: Polymer Chemistry, Jan. 1, 2009, vol. 47, pp. 1696-1705.
Ma J et al., "Synthesis and Solution-State Assembly or Buld State Thiol-ene Crosslinking of Pyrrolidinone- and Alkene-Functionalized Amphiphilic Block Fluorocopoplymers: From Functional Nanoparticles to Anti-Fouling Coatings", Australian Journal of Chemistry: An International Journal for Chemical Sci, Jan. 1, 2010, pp. 1159-1163, vol. 63, No. 8,C S I R O Publishing, Australia.
Mori H. et al., "Synthesis and Surface Characterization of Hydrophilic-Hydrophobic Block Copolymers Containing Poly(2,3-dihydroxypropyl methacrylate)," Macromolecules, American Chemical Society, US, vol. 27, No. 15, Jul. 18, 1994, pp. 4093-9297; XP000456650, DOI: 102021/MA00093A010.
S. Chavda et al., "Synthesis of stimuli responsive PEG47-b-PAA126-b-PSt32 triblock copolymer and its self-assembly in aqueous solutions", European Polymer Journal, Sep. 2012, vol. 49, pp. 209-216.
Sachin Borkar et al., "New Highly Fluorinated Styrene-Based Materials with Low Surface Energy Prepared by ATRP", Macromolecules, Jan. 2004, vol. 37, pp. 788-794.
Segalman R.A. et al., "Graphoepitaxy of Spherical Domain Block Copolymer Films," Advanced Materials, Wiley-VCH Verlag GmbH & Co. KGAA, DE, vol. 13, No. 15, Aug. 3, 2001, pp. 1152-1155; XP001129643.
Truelsen et al., "Synthesis by ATRP of triblock copolymers with densely grafted styrenic end blocks from a polyisobutylene macroinitiator", Marcomol. Rapid. Commun., Jul. 2, 1999, vol. 21, No. 2, pp. 1-5.
EESR for EP Application No. 15847536.8 dated Aug. 23, 2018, 6 pages.
Chakrabarty, et al., "Tailor-Made Polyfluoroacrylate and its Block Copolymer by RAFT Polymerization in Miniemulsion; Improved Hydrophobicity in the Core-Shell Block Copolymer", Journal of Colloid and Interface Science, vol. 408, Oct. 2013, pp. 66-74.
Gregory, et al., "Complex Polymer Architectures via RAFT Polymerization: From Fundamental Process to Extending the Scope Using Click Chemistry and Nature's Building Blocks", Progress in Polymer Science, vol. 37, No. 1, Jan. 2012, pp. 38-105.

* cited by examiner

BLOCK COPOLYMER

CROSS-REFERENCE TO RELATED APPLICATION

This application is a national phase entry under 35 U.S.C. § 371 of International Application No. PCT/KR2014/012027, filed Dec. 8, 2014, which claims priority to Korean Patent Application No. 10-2013-0151866, filed Dec. 6, 2013, Korean Patent Application No. 10-2013-0151865, filed Dec. 6, 2013, Korean Patent Application No. 10-2013-0151867, filed Dec. 6, 2013, Korean Patent Application No. 10-2013-0159994, filed Dec. 20, 2013, Korean Patent Application No. 10-2014-0131964, filed Sep. 30, 2014 and Korean Patent Application No. 10-2014-0175406, filed Dec. 8, 2014, the disclosures of which are incorporated herein by reference.

TECHNICAL FIELD

The present application relates to a block copolymer.

BACKGROUND

Block copolymers have molecular structures in which polymer subunits having chemically different structures from each other are linked by covalent bonds. Block copolymers are capable of forming periodically aligned structure such as the sphere, the cylinder or the lamella through phase separations. Sizes of domains of the structures formed by the self assemblies of block copolymers may be adjusted in a wide range, and various shapes of structures can be prepared. Therefore, they can be utilized in pattern-forming methods by lithography, various magnetic recording mediae or next generation nano devices such as metal dots, quantum dots or nano lines, high density magnetic storage mediae, and the like.

DESCRIPTION

Technical Object

The present application provides a block copolymer and its application.

Technical Solution

The term "alkyl group" as used herein may refer to, unless defined otherwise, an alkyl group having 1 to 20, 1 to 16, 1 to 12, 1 to 8, or 1 to 4 carbon atoms. The alkyl group may have a linear, branched or cyclic structure, and may be optionally substituted with at least one substituent.

The term "alkoxy group" as used herein may refer to, unless defined otherwise, an alkoxy group having 1 to 20, 1 to 16, 1 to 12, 1 to 8, or 1 to 4 carbon atoms. The alkoxy group may have a linear, branched, or cyclic structure, and may be optionally substituted with at least one substituent.

The term "alkenyl or alkynyl group" as used herein may refer to, unless defined otherwise, an alkenyl or alkynyl group having 2 to 20, 2 to 16, 2 to 12, 2 to 8, or 2 to 4 carbon atoms. The alkenyl or alkynyl group may have a linear, branched, or cyclic structure, and may be optionally substituted with at least one substituent.

The term "alkylene group" as used herein may refer to, unless defined otherwise, an alkylene group having 1 to 20, 1 to 16, 1 to 12, 1 to 8 or 1 to 4 carbon atoms. The alkylene group may have a linear, branched, or cyclic structure, and may be optionally substituted with at least one substituent.

The term "alkenylene or alkynylene group" as used herein may refer to, unless defined otherwise, an alkenylene or alkynylene group having 2 to 20, 2 to 16, 2 to 12, 2 to 8 or 2 to 4 carbon atoms. The alkenylene or alkynylene group may have a linear, branched, or cyclic structure, and may be optionally substituted with at least one substituent.

The term "aryl or arylene group" as used herein may be, unless defined otherwise, a monovalent or bivalent substituent derived from a compound including one benzene ring structure or a structure, in which at least two benzene rings are linked with sharing one or two carbon atoms or by an optional linker, or a derivative of the compound. The aryl or arylene group may be, unless defined otherwise, an aryl group having 6 to 30, 6 to 25, 6 to 21, 6 to 18, or 6 to 13 carbon atoms.

The term "aromatic structure" as used herein may refer to the aryl group or the arylene group.

The term "alicyclic structure" as used herein may refer to, unless defined otherwise, a cyclic hydrocarbon structure that is not the aromatic cyclic structure. The alicyclic structure may be, unless defined otherwise, a structure having 3 to 30, 3 to 25, 3 to 21, 3 to 18 or 3 to 13 carbon atoms.

The term "single bond" as used herein may refer to a case where there is no atom in a corresponding site. For example, a case where "B" is a single bond in the structure represented by "A-B-C," means that there is no atom in the "B" position and therefore the structure represented by "A-C" is formed by the "A" directly connecting to the "C."

A substituent that may optionally substitute for the alkyl group, the alkenyl group, the alkynyl group, the alkylene group, the alkenylene group, the alkynylene group, the alkoxy group, the aryl group, the arylene group, a chain, the aromatic structure, and the like may be hydroxyl group, halogen atom, carboxyl group, glycidyl group, acryloyl group, methacryloyl group, acryloyloxy group, methacryloyloxy group, thiol group, alkyl group, alkenyl group, alkynyl group, alkylene group, alkenylene group, alkynylene group, alkoxy group or aryl group, but is not limited thereto.

In one embodiment, a monomer as represented by Formula 1 below that have a novel structure and that is capable of forming block copolymers may be provided.

[Formula 1]

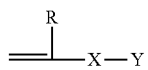

In Formula 1, the R is hydrogen or an alkyl group and the X is the single bond, the oxygen atom, the sulfur atom, —S(=O)$_2$—, the carbonyl group, the alkylene group, the alkenylene group, the alkynylene group, —C(=O)—X$_1$— or —X$_1$—C(=O)—. In the above, the X$_1$ may be the oxygen atom, the sulfur atom, —S(=O)$_2$—, the alkylene group, the alkenylene group or the alkynylene group, and the Y may be a monovalent substituent including a cyclic structure to which a chain having 8 or more chain-forming atoms is linked.

In another embodiment, in the Formula 1, the X may be the single bond, the oxygen atom, the carbonyl group, —C(=O)—O— or —O—C(=O)—; or the X may be —C(=O)—O—, but is not limited thereto.

In Formula 1, the monovalent substituent Y includes a chain structure formed by at least 8 chain-forming atoms.

The term "chain-forming atoms" as used herein refers to atoms forming a linear structure of a certain chain. The chain may have a linear or branched structure; however the number of the chain-forming atoms is calculated only by the number of atoms forming the longest linear chain. Therefore, other atoms such as, in a case where the chain-forming atom is the carbon atom, the hydrogen atom that is linked to the carbon atom and the like are not calculated as the number of the chain-forming atoms. Further, in case of the branched chain, the number of the chain-forming atoms is the number of atoms forming the longest chain. For example, the chain is n-pentyl, all of the chain-forming atoms are carbon atoms and the number thereof is 5. If the chain is 2-methylpentyl, all of the chain-forming atoms are also carbon atoms and the number thereof is 5. The chain-forming atoms may be the carbon, the oxygen, the sulfur or the nitrogen, and the like and appropriate chain-forming atoms may be the carbon, the oxygen or the nitrogen; or the carbon or the oxygen. The number of the chain-forming atoms may be 8 or more, 9 or more, 10 or more, 11 or more; or 12 or more. The number of the chain-forming atoms may be 30 or less, 25 or less, 20 or less or 16 or less.

When the compound of the Formula 1 forms a block copolymer, the block copolymer may show an excellent self-assembly properties due to the presence of the chain.

In one embodiment, the chain may be a linear hydrocarbon chain such as a linear alkyl group. In this case, the alkyl group may be an alkyl group having 8 or more, 8 to 30, 8 to 25, 8 to 20 or 8 to 16 carbon atoms. At least one carbon atom of the alkyl group may be optionally substituted with the oxygen atom, and at least one hydrogen atom of the alkyl group may be optionally substituted with another substituent.

In Formula 1, the Y may include a cyclic structure. The chain may be linked to the cyclic structure. The self assembly properties of block copolymers formed by the compound may be further improved due to the cyclic structure. The cyclic structure may be the aromatic structure or the alicyclic structure.

The chain may be directly linked to the cyclic structure or may be linked to the cyclic structure via a linker. As the linker, the oxygen atom, the sulfur atom, —$NR_1$—, —$S(=O)_2$—, the carbonyl group, the alkylene group, the alkenylene group, the alkynylene group, —$C(=O)$—$X_1$— or —$X_1$—$C(=O)$— may be illustrated. In the above, the $R_1$ may be the hydrogen, the alkyl group, the alkenyl group, the alkynyl group, the alkoxy group or the aryl group and the X1 may be the single bond, the oxygen atom, the sulfur atom, —$NR_2$—, —$S(=O)_2$—, the alkylene group, the alkenylene group or the alkynylene group and, in the above, the $R_2$ may be the hydrogen, the alkyl group, the alkenyl group, the alkynyl group, the alkoxy group or the aryl group. An appropriate linker may be the oxygen atom or the nitrogen atom. For example, the chain may be linked to the aromatic structure via the oxygen atom or the nitrogen atom. In this case, the linker may be the oxygen atom or the —$NR_1$—, where the $R_1$ may be the hydrogen, the alkyl group, the alkenyl group, the alkynyl group, the alkoxy group or the aryl group.

In one embodiment, the Y of the Formula 1 may be represented by Formula 2 below.

—P-Q-Z [Formula 2]

In Formula 2, the P may be the arylene group, the Q may be the single bond, the oxygen atom or —$NR_3$—, where the $R_3$ may be the hydrogen, the alkyl group, the alkenyl group, the alkynyl group, the alkoxy group or the aryl group, and the Z may be the chain having at least 8 chain-forming atoms. In case where the Y of the Formula 1 is the substituent of the Formula 2, the P of the Formula 2 may be directly linked to the X of the Formula 1.

In Formula 2, an appropriate P may be an arylene group having 6 to 12 carbon atoms such as the phenylene group, but is not limited thereto.

In Formula 2, an appropriate Q may be the oxygen atom or —$NR_1$—, where the $R_1$ may be the hydrogen, the alkyl group, the alkenyl group, the alkynyl group, the alkoxy group or the aryl group.

As an appropriate embodiment of the monomer of Formula 1, a monomer of Formula 1, in which the R is the hydrogen atom or the alkyl group; or the hydrogen atom or the alkyl group having 1 to 4 carbon atom(s), the X is —$C(=O)$—O— and the Y is the substituent of Formula 2, in which the P is the arylene having 6 to 12 carbon atoms or phenylene group, the Q is the oxygen atom and the Z is the chain having 8 or more chain-forming atoms may be illustrated.

Therefore, as an appropriate embodiment, a monomer of Formula 3 below may be illustrated.

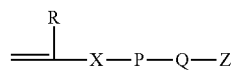

[Formula 3]

In Formula 3, the R is the hydrogen atom or the alkyl group having 1 to 4 carbon atom(s), the X is —$C(=O)$—O—, the P is the arylene group having 6 to 12 carbon atoms, Q is the oxygen atom, and Z is the above-described chain having 8 or more chain-forming atoms.

Another embodiment of the present application relates to a method for preparing a block copolymer comprising a step of forming a block by polymerizing the monomer.

A specific method for preparing the block copolymer is not particularly limited, as long as it comprises a step forming at least one block of the block copolymer by using the above-described monomer.

For example, the block copolymer may be prepared by a living radical polymerization (LRP) using the monomer. For example, there are methods such as the anionic polymerization, in which block copolymers are synthesized in the presence of inorganic acid salts such as salts of alkali metal or alkali earth metal by using organic rare earth metal complexes or organic alkali metal compounds as polymerization initiators; the anionic polymerization, in which block copolymers are synthesized in the presence of organic aluminum compounds by using organic alkali metal compounds as polymerization initiators; the atom-transfer radical polymerization (ATRP) using an atom transfer radical polymerizer as a polymerization controller; the activators regenerated by electron transfer (ATGET) ATRP performing polymerization in the presence of an organic or inorganic reducing agent generating electrons using an atom transfer radical polymerizer as a polymerization controller; the initiators for continuous activator regeneration (ICAR) ATRP; the reversible addition-ring opening chain transfer (RAFT) polymerization using an inorganic reducing agent reversible addition-ring opening chain transfer agent; and the a method using an organic tellurium compound as an initiator, and an appropriate method may be selected among the above methods.

In one embodiment, the block copolymer may be prepared by a method including polymerizing a material comprising monomers capable of forming the block in the presence of radical initiators and living radical polymerization reagents by the living radical polymerization.

In the preparation of the block copolymer, a method for forming other block included in the block copolymer along with the block formed by the above monomer is not particularly limited, and the other block may be formed by selecting appropriate monomers considering the kind of blocks to be formed.

The method for preparing the block copolymer may further include precipitating a polymerized product produced by the above-described process in a non-solvent.

A kind of the radical initiators may be suitably selected in consideration of polymerization efficiency without particular limitation, and an azo compound such as azobisisobutyronitrile (AIBN) or 2,2'-azobis-(2,4-dimethylvaleronitrile), or a peroxide compound such as benzoyl peroxide (BPO) or di-t-butyl peroxide (DTBP) may be used.

The LRP may be performed in a solvent such as methylenechloride, 1,2-dichloroethane, chlorobenzene, dichlorobenzene, benzene, toluene, acetone, chloroform, tetrahydrofuran, dioxane, monoglyme, diglyme, dimethylformamide, dimethylsulfoxide or dimethylacetamide.

As the non-solvent, for example, an alcohol such as methanol, ethanol, normal propanol or isopropanol, a glycol such as ethyleneglycol, or an ether compound such as n-hexane, cyclohexane, n-heptane or petroleum ether may be used without limitation.

Another embodiment of the present application relates to a block copolymer including a block (hereinafter, may be referred to as a first block) formed by using the monomer.

The block may be represented by, for example, Formula 4.

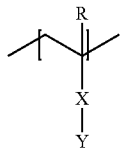

[Formula 4]

In the Formula 4, the R, X and Y may be the same as described regarding the R, X and Y of the Formula 1, respectively.

Therefore, in Formula 4, the R may be hydrogen or an alkyl group having 1 to 4 carbon atom(s), the X may be the single bond, the oxygen atom, the sulfur atom, $-S(=O)_2-$, the carbonyl group, the alkylene group, the alkenylene group, the alkynylene group, $-C(=O)-X_1-$ or $-X_1-C(=O)-$, wherein the $X_1$ may be the oxygen atom, the sulfur atom, $-S(=O)_2-$, the alkylene group, the alkenylene group or the alkynylene group, and the Y may be a monovalent substituent including a cyclic structure to which a chain having 8 or more chain-forming atoms is linked. As for a specific type of above each substituent, the above description may be applied in the same manner.

In one embodiment, the first block may be a block of the Formula 4, in which the R is the hydrogen or the alkyl group; or the hydrogen or the alkyl group having 1 to 4 carbon atom(s), the X is $-C(=O)-O-$, and the Y is the substituent represented by Formula 2. Such a block may be referred to as a 1A block, but is not limited thereto. This block may be represented by the Formula 5 below.

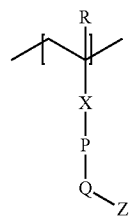

[Formula 5]

In Formula 5, the R may be the hydrogen atom or the alkyl group having 1 to 4 carbon atom(s), the X may be the single bond, the oxygen atom, $-C(=O)-O-$ or $-O-C(=O)-$, the P may be the arylene group, the Q may be the oxygen atom or $-NR_3-$, where the $R_3$ may be the hydrogen, the alkyl group, the alkenyl group, the alkynyl group, the alkoxy group or the aryl group, the Z is the chain having 8 or more chain-forming atoms. In another embodiment, the Q of the Formula 5 may be the oxygen atom.

In another embodiment, the first block may be a block represented by Formula 6. Such a first block may be referred to as a 1B block herein.

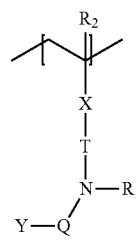

[Formula 6]

In Formula 6, $R_1$ and $R_2$ may be each independently hydrogen or an alkyl group having 1 to 4 carbon atom(s), the X may be the single bond, the oxygen atom, the sulfur atom, $-S(=O)_2-$, the carbonyl group, the alkylene group, the alkenylene group, the alkynylene group, $-C(=O)-X_1-$ or $-X_1-C(=O)-$, in which the $X_1$ may be the single bond, the oxygen atom, the sulfur atom, $-S(=O)_2-$, the alkylene group, the alkenylene group or the alkynylene group, the T may be the single bond or the arylene group, the Q may be the single bond or the carbonyl group and the Y may be the chain having at least 8 chain-forming atoms.

In the 1B block of Formula 6, X may be the single bond, the oxygen atom, the carbonyl group, $-C(=O)-O-$ or $-O-C(=O)-$.

As a particular embodiment of the chain Y in the 1B block, the above description regarding Formula 1 may be applied thereto in a similar manner.

In another embodiment, the first block may be a block represented by at least one of the Formulas 4 to 6, in which the electronegativity of at least one chain-forming atom of the chain having 8 or more chain-forming atoms is 3 or more. The electronegativity of the chain-forming atom may be 3.7 or less in another embodiment. Herein, such a block may be referred to as a 1C block. As the atom having the electronegativity of 3 or more, the nitrogen atom or the oxygen atom may be illustrated, but is not limited thereto.

Kinds of another block (hereinafter, may be referred to as a second block) included in the block copolymer along with the first block such as the 1A, 1B or 1C block is not particularly limited.

For example, the second block may be polyvinylpyrrolidone block, polylactic acid block, polyvinylpyridine block, polystyrene block such as polystyrene block or polytrimethylsilylstyrene, polyalkyleneoxide block such as polyethyleneoxide block, or polyolefin block such as polyethylene block or polyisoprene block or polybutadiene block. Such a block used herein may be referred to as a 2A block.

In one embodiment, the second block included along with the first block such as the 1A, 1B or 1C block in the block copolymer may be a block including the aromatic structure comprising at least one halogen atom.

Such a second block may be, for example, represented by the Formula 7 below and may be referred to as a 2B block.

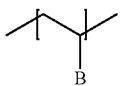

[Formula 7]

In Formula 7, the B may be a monovalent substituent having an aromatic structure including at least one halogen atom.

Such a second block may be effectively interacted with the above-described first block such that the block copolymer can have an excellent self assembling characteristic.

The aromatic structure of Formula 7 may be, for example, an aromatic structure having 6 to 18 or 6 to 12 carbon atoms.

Further, the halogen atom included in Formula 7 may be, but is not limited to, the fluorine atom or the chloride atom, and appropriately the fluorine atom.

In one embodiment, the B of Formula 7 may be a monovalent substituent having an aromatic structure having 6 to 12 carbon atoms, which is substituted with 1 or more, 2 or more, 3 or more, 4 or more, or 5 or more halogen atoms. The upper limit of the number of halogen atoms is not particular limited, but there may be 10 or less, 9 or less, 8 or less, 7 or less, or 6 or less halogen atoms.

For example, the block represented by the Formula 7, which is the 2B block, may be represented by the Formula 8 below.

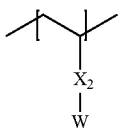

[Formula 8]

In Formula 8, the $X_2$ may be the single bond, the oxygen atom, the sulfur atom, —S(=O)$_2$—, the alkylene group, the alkenylene group, the alkynylene group, —C(=O)—$X_1$— or —$X_1$—C(=O)—, in which the $X_1$ is the single bond, the oxygen atom, the sulfur atom, —S(=O)$_2$—, the alkylene group, the alkenylene group or the alkynylene group, and the W may be an aryl group substituted with at least one halogen atom. In the above, the W may be an aryl group, substituted with at least one halogen atom, for example, an aryl group that has 6 to 12 carbon atoms and that is substituted with 2 or more, 3 or more, 4 or more, or 5 or more halogen atoms.

The 2B block may be, for example, represented by the Formula 9 below.

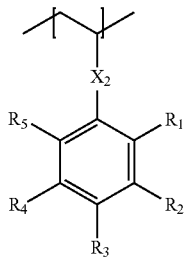

[Formula 9]

In Formula 9, the $X_2$ may be the single bond, the oxygen atom, the sulfur atom, —S(=O)$_2$—, the alkylene group, the alkenylene group, the alkynylene group, —C(=O)—$X_1$— or —$X_1$—C(=O)—, in which the $X_1$ is the single bond, the oxygen atom, the sulfur atom, —S(=O)$_2$—, the alkylene group, the alkenylene group or the alkynylene group, and the $R_1$ to $R_5$ may be each independently hydrogen, an alkyl group, a haloalkyl group or a halogen atom. The number of the halogen atom included in the $R_1$ to $R_5$ is 1 or more.

In Formula 9, in another embodiment, the $X_2$ may be the single bond, the oxygen atom, the alkylene group, —C(=O)—O— or —O—C(=O)—.

In Formula 9, the $R_1$ to $R_5$ may be each independently hydrogen, an alkyl group, a haloalkyl group or a halogen atom, and the $R_1$ to $R_5$ may include 1 or more, 2 or more, 3 or more, 4 or more, or 5 or more halogen atom(s) such as fluorine atom(s). The number of the halogen atom(s) such as the fluorine atom(s) included in the $R_1$ to $R_5$ may be, for example, 10 or less, 9 or less, 8 or less, 7 or less, 6 or less.

In one embodiment, the second block may be a block represented by Formula 10. Such a block used herein may be referred to as a 2C block.

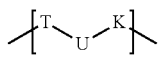

[Formula 10]

In Formula 10, the T and K may be each independently the oxygen atom or the single bond, and the U may be the alkylene group.

In one embodiment, in the 2C block, the U of Formula 10 may be the alkylene group having 1 to 20, 1 to 16, 1 to 12, 1 to 8 or 1 to 4 carbon atom(s).

In another embodiment, the 2C block may be a block of the Formula 10, in which one of the T and K of the Formula 10 is the single bond, and the other of the T and K of the Formula 10 is the oxygen atom. In the above block, the U may be the alkylene group having 1 to 20, 1 to 16, 1 to 12, 1 to 8 or 1 to 4 carbon atom(s).

In still another embodiment, the 2C block may be a block of the Formula 10, in which both of the T and K of the Formula 10 are the oxygen atoms. In the above block, the U may be the alkylene group having 1 to 20, 1 to 16, 1 to 12, 1 to 8 or 1 to 4 carbon atom(s).

In still another embodiment, the second block may be a block including at least one metal atom or metalloid atom. Such a block may be referred to as a 2D block. This block may improve etching selectivity when an etching process is performed with respect to, for example, a film including a self-assembled block copolymer.

The metal atom or metalloid atom in the 2D block may be a silicon atom, an iron atom or a boron atom, but is not particularly limited as long as it may exhibit suitable etching selectivity due to a difference with another atom in the block copolymer.

The 2D block may include 1 or more, 2 or more, 3 or more, 4 or more, or 5 or more halogen atoms, for example, fluorine atoms, along with the metal or metalloid atom. The 2D block may include 10 or less, 9 or less, 8 or less, 7 or less, or 6 or less halogen atoms such as fluorine atoms.

The 2D block may be represented by Formula 11.

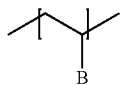

[Formula 11]

In Formula 11, the B may be a monovalent substituent having an aromatic structure including a halogen atom and a substituent having the metal atom or the metalloid atom.

The aromatic structure of Formula 11 may be an aromatic structure having 6 to 12 carbon atoms, for example, an aryl group or an arylene group.

The 2D block of the Formula 11 may be represented by the Formula 12 below.

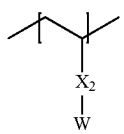

[Formula 12]

In Formula 12, the $X_2$ may be the single bond, the oxygen atom, the sulfur atom, $-NR_1-$, $-S(=O)_2-$, the alkylene group, the alkenylene group, the alkynylene group, $-C(=O)-X_1-$ or $-X_1-C(=O)-$, in which the $R_1$ is the hydrogen, the alkyl group, the alkenyl group, the alkynyl group, the alkoxy group or the aryl group, and the $X_1$ is the single bond, the oxygen atom, the sulfur atom, $-NR_2-$, $-S(=O)_2-$, the alkylene group, the alkenylene group or the alkynylene group, and the W may be an aryl group including at least one halogen atom and a substituent including the metal atom or the metalloid atom.

In the above, the W may be an aryl group that has 6 to 12 carbon atoms and that includes at least one halogen atom and a substituent including the metal atom or the metalloid atom.

The aryl group may include at least one or 1 to 3 substituents including the metal atom or metalloid atom, and 1 or more, 2 or more, 3 or more, 4 or more, or 5 or more halogen atom(s).

10 or less, 9 or less, 8 or less, 7 or less, or 6 or less halogen atoms may be included therein.

The 2D block of the Formula 12 may be represented by the Formula 13 below.

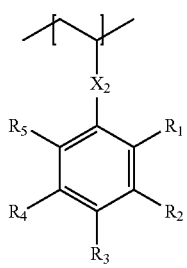

[Formula 13]

In Formula 13, the $X_2$ may be the single bond, the oxygen atom, the sulfur atom, $-NR_1-$, $-S(=O)_2-$, the alkylene group, the alkenylene group, the alkynylene group, $-C(=O)-X_1-$ or $-X_1-C(=O)-$, in which the $R_1$ may be the hydrogen, the alkyl group, the alkenyl group, the alkynyl group, the alkoxy group or the aryl group, and the $X_1$ may be the single bond, the oxygen atom, the sulfur atom, $-NR_2-$, $-S(=O)_2-$, the alkylene group, the alkenylene group or the alkynylene group, the $R_1$ to $R_5$ may be each independently the hydrogen, the alkyl group, the haloalkyl group, the halogen atom or the substituent including the metal or the metalloid atom, with the provision that at least one of $R_1$ to $R_5$ includes a halogen atom, and at least one of $R_1$ to $R_5$ is the substituent including the metal or the metalloid atom.

In the Formula 13, 1 or more, 1 to 3 or 1 to 2 of the $R_1$ to $R_5$ may be the substituent including the metal or the metalloid atom.

In the Formula 13, in the $R_1$ to $R_5$, 1 or more, 2 or more, 3 or more, 4 or more or 5 or more halogen atom(s) may be included. The number of the halogen atom(s) included in the $R_1$ to $R_5$ may by 10 or less, 9 or less, 8 or less, 7 or less, or 6 or less.

The substituent including the metal or the metalloid atom described above may be carboranyl group or silsesquioxanyl group such as polyhedral oligomeric silsesquioxanyl, ferrocenyl group or trialkylsiloxy group. However, they are not particularly limited, as long as they are selected so as to obtain the etching selectivity by including at least one metal or metalloid atom.

In yet another embodiment, the second block may be a block including an atom which is an atom having the electronegativity of 3 or more and which is an atom (hereinafter, referred to as a non-halogenic atom) that is not the halogen atom. Such a block may be referred to as a 2E block. In another embodiment, the electronegativity of the non-halogenic atom in the 2E block may be 3.7 or less.

The non-halogenic atom in the 2E block may be, but is not limited to, a nitrogen atom or an oxygen atom.

The 2E block may include, along with the non-halogenic atom having an electronegativity of 3 or more, 1 or more, 2 or more, 3 or more, 4 or more, or 5 or more halogen atoms, for example, fluorine atoms. The number of the halogen atom(s) such as the fluorine atom(s) in the 2E block may include 10 or less, 9 or less, 8 or less, 7 or less, or 6 or less.

The 2E block may be represented by Formula 14.

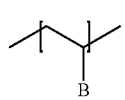

[Formula 14]

In Formula 14, the B may be a monovalent substituent having an aromatic structure that includes a substituent including the non-halogenic atom having an electronegativity of 3 or more and that includes the halogen atom.

The aromatic structure of Formula 14 may be an aromatic structure having 6 to 12 carbon atoms, for example, an aryl group or an arylene group.

In another embodiment, the block of the Formula 14 may be represented by the Formula 15 below.

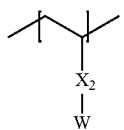

[Formula 15]

In Formula 15, the $X_2$ may be the single bond, the oxygen atom, the sulfur atom, —S(=O)$_2$—, the alkylene group, the alkenylene group, the alkynylene group, —C(=O)—X$_1$— or —X$_1$—C(=O)—, in which the $R_1$ may be the hydrogen, the alkyl group, the alkenyl group, the alkynyl group, the alkoxy group or the aryl group, and the $X_1$ may be the single bond, the oxygen atom, the sulfur atom, —NR$_2$—, —S(=O)$_2$—, the alkylene group, the alkenylene group or the alkynylene group, and the W may be the aryl group including the substituent including the non-halogenic atom having an electronegativity of 3 or more and at least one halogen atom.

In the above, the W may be an aryl group that has 6 to 12 carbon atoms, that includes the substituent including the non-halogenic atom having the electronegativity of 3 or more and that includes at least one halogen atom.

Such an aryl group may include at least one or 1 to 3 substituents including the non-halogenic atom having the electronegativity of 3 or more. In addition, the aryl group may include 1 or more, 2 or more, 3 or more, 4 or more, or 5 or more halogen atom(s). In the above, the aryl group may include 10 or less, 9 or less, 8 or less, 7 or less, or 6 or less halogen atoms.

In another embodiment, the block of the Formula 15 may be represented by the Formula 16.

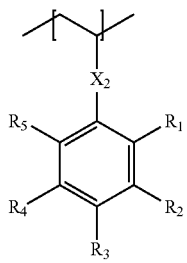

[Formula 16]

In Formula 16, the $X_2$ may be the single bond, the oxygen atom, the sulfur atom, —NR$_1$—, —S(=O)$_2$—, the alkylene group, the alkenylene group, the alkynylene group, —C(=O)—X$_1$— or —X$_1$—C(=O)—, in which the $R_1$ may be hydrogen, the alkyl group, the alkenyl group, the alkynyl group, the alkoxy group or the aryl group, and the $X_1$ may be the single bond, the oxygen atom, the sulfur atom, —NR$_2$—, —S(=O)$_2$—, the alkylene group, the alkenylene group or the alkynylene group, and the $R_1$ to $R_5$ may be each independently hydrogen, the alkyl group, the haloalkyl group, the halogen atom and the substituent including the non-halogenic atom having the electronegativity of 3 or more. In the above, at least one of the $R_1$ to $R_5$ is the halogen atom, and at least one of the $R_1$ to $R_5$ is the substituent including the non-halogenic atom having the electronegativity of 3 or more.

In Formula 16, at least one, 1 to 3, or 1 to 2 of the $R_1$ to $R_5$ may be the above-described substituents including the non-halogenic atom having the electronegativity of 3 or more.

In Formula 16, the $R_1$ to $R_5$ may include 1 or more, 2 or more, 3 or more, 4 or more, or 5 or more halogen atoms. The $R_1$ to $R_5$ may include 10 or less, 9 or less, 8 or less, 7 or less, or 6 or less halogen atoms.

The substituent including the non-halogenic atom having the electronegativity of 3 or more described above may be, but is not limited to, the hydroxyl group, the alkoxy group, the carboxyl group, the amido group, the ethylene oxide group, the nitrile group, the pyridine group or the amino group.

In another embodiment, the second block may include an aromatic structure having a heterocyclic substituent. Such a second block may be referred to as a 2F block herein.

The 2F block may be represented by Formula 17.

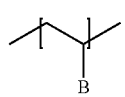

[Formula 17]

In Formula 17, the B may be a monovalent substituent having an aromatic structure that has 6 to 12 carbon atoms and that is substituted with a heterocyclic substituent.

If necessary, the aromatic structure of Formula 17 may include at least one halogen atom.

The block of the Formula 17 may be represented by the Formula 18.

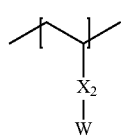

[Formula 18]

In Formula 18, the $X_2$ may be the single bond, the oxygen atom, the sulfur atom, —NR$_1$—, —S(=O)$_2$—, the alkylene group, the alkenylene group, the alkynylene group, —C(=O)—X$_1$— or —X$_1$—C(=O)—, in which the $R_1$ may be hydrogen, the alkyl group, the alkenyl group, the alkynyl group, the alkoxy group or the aryl group, and the $X_1$ may be the single bond, the oxygen atom, the sulfur atom, —NR$_2$—, —S(=O)$_2$—, the alkylene group, the alkenylene group or the alkynylene group, and the W may be an aryl group that has 6 to 12 carbon atoms and that has the heterocyclic substituent.

The block of the Formula 18 may be represented by Formula 19.

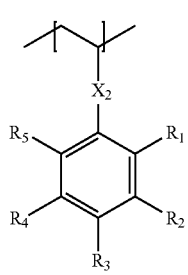

[Formula 19]

In Formula 19, the $X_2$ may be the single bond, the oxygen atom, the sulfur atom, —NR$_1$—, —S(=O)$_2$—, the alkylene group, the alkenylene group, the alkynylene group, —C(=O)—$X_1$— or —$X_1$—C(=O)—, in which the $R_1$ may be hydrogen, the alkyl group, the alkenyl group, the alkynyl group, the alkoxy group or the aryl group, and the $X_1$ may be the single bond, the oxygen atom, the sulfur atom, —$NR_2$—, —$S(=O)_2$—, the alkylene group, the alkenylene group or the alkynylene group, and the $R_1$ to $R_5$ may be each independently hydrogen, the alkyl group, the haloalkyl group, the halogen atom or the heterocyclic substituent. In the above, at least one of the $R_1$ to $R_5$ is the heterocyclic substituent.

In Formula 19, at least one, for example, 1 to 3 or 1 to 2 of the $R_1$ to $R_5$ may be the heterocyclic substituent, and the other(s) may be the hydrogen atom, the alkyl group or the halogen atom; or the hydrogen atom or the halogen atom; or the hydrogen atom.

The above-described heterocyclic substituent may be, but is not limited to, a substituent derived from phthalimide, a substituent derived from thiopene, a substituent derived from thiazole, a substituent derived from carbazole or a substituent derived from imidazole.

The block copolymer of the present application may include at least one of the above-described first blocks, and at least one of the above-described second blocks. Such a block copolymer may include 2 or 3 blocks, or 3 or more blocks. In one embodiment, the block copolymer may be a diblock copolymer including any one of the first blocks and any one of the second blocks.

Such a block copolymer may show excellent self assembling properties or phase separation properties fundamentally. Further, if the selection of and the combination of the blocks is performed so as for the block copolymer to satisfy at least one parameter among ones described below, the self assembling properties or phase separation properties may further improved.

Block copolymers may be phase-separated, since they comprise two or more polymer chains linked to each other via covalent bonds. The block copolymer of the present application shows excellent phase separation properties, if necessary, may form nano scaled structure by a microphase separation. The shape or size of the nano scaled structure may be controlled by the size (the molecular weight and the like) of the block copolymer or relative ratios of blocks. The structure formed by the phase separation may include the sphere, the cylinder, the gyroid, the lamella and the reversed structure, and the ability forming the above structure may be referred to as a self assembling properties. The present inventors have confirmed that, among the above various block copolymers having various structures, the block copolymer satisfying at least one parameter among ones described below can show further improved self assembling properties that the block copolymers fundamentally have. The block copolymer may satisfy one parameter among ones described below or two or more parameters among ones described below. Specially, it is confirmed that it is possible to make the block copolymer to show a vertically aligning property by the block copolymer satisfying an appropriate parameter. The term "vertically aligning property" as used herein may refer to aligning property of the block copolymer and may refer to a case where the nano scaled structure formed by the block copolymer is aligned vertically to a direction of a substrate. Techniques controlling an aligning of a self assembled structure of a block copolymer to be vertical or parallel with respect to various substrates are a big part of practical application of a block copolymer. Conventionally, the aligning of the nano scaled structure in a layer of a block copolymer depends on what block among blocks forming the block copolymer is exposed to a surface or an air. Generally, since lots of substrates are polar and the air is non-polar, a block having more polarity than the other block in the block copolymer wets on the substrate and a block having less polarity than the other block in the block copolymer wets with respect to the interface between the air. Therefore, many techniques are proposed in order for blocks of a block copolymer having properties different from each other to wet simultaneously toward the substrate, and a most typical method is to control the aligning by preparing the neutral surface. However, in one embodiment, by controlling the parameters below, the block copolymer may be vertically aligned with respect to substrates, to which conventionally known treatment for accomplishing the vertical alignment including the neutral surface treatment is not performed. Further, in an additional embodiment, the vertical alignment may be accomplished with respect to a large area in a short time by a thermal annealing.

In one embodiment, the block copolymer may form a layer showing an in-plane phase diffraction pattern of the grazing incidence small angle X ray scattering (GISAXS) on a hydrophobic surface. The block copolymer may form a layer showing an in-plane phase diffraction pattern of the grazing incidence small angle X ray scattering (GISAXS) on a hydrophilic surface.

The term "showing the in-plane phase diffraction pattern of the grazing incidence small angle X ray scattering (GISAXS)" as used herein may refer to a case where a peak vertical to the X coordinate is observed in the GISAXS diffraction pattern when the GISAXS analysis is performed. Such a peak may be confirmed by the vertical aligning property of the block copolymer. Therefore, the block copolymer showing the in-plane phase diffraction pattern shows the vertical aligning property. In further embodiment, two or more peaks may be observed in the X coordinate of the GISAXS diffraction pattern. In case where two or more peaks are observed, the scattering vectors (the q values) may be confirmed with having constant ratios, and in the above case, the phase separation efficiency may be further improved.

The term "vertical" as used herein is a term considering errors and, for example, it may include errors within ±10 degrees, ±8 degrees, ±6 degrees, ±4 degrees or ±2 degrees.

A block copolymer capable of forming a layer showing the in-plane phase diffraction patterns on both of the hydrophobic and the hydrophilic surfaces can show the vertical aligning property on various surface to which any treatment for inducing the vertical aligning is not performed. The term "hydrophobic surface" as used herein may refer to a surface of which a wetting angle of purified water is in a range from 5 degrees to 20 degrees. Examples of the hydrophobic surface may include a surface of silicone treated with the piranha solution, sulfuric acid, or an oxygen plasma, but is not limited thereto. The term "hydrophilic surface" as used herein may refer to a surface of which a wetting angle of purified water is in a range from 50 degrees to 70 degrees. Examples of the hydrophilic surface may include a surface of silicone treated with hydrogen fluoride, silicone treated with hexamethyldisilazane or polydimethylsiloxane treated with oxygen plasma, but is not limited thereto.

Unless defined otherwise, in this document, a property such as a wetting angle that can be changed according to temperature is measured at room temperature. The term "room temperature" as used herein may refer to a temperature in its natural state that is not heated and cooled and may refer to a temperature in a range from about 10° C. to 30° C., or of about 25° C. or about 23° C.

The layer that is formed on the hydrophobic or hydrophilic surface and shows the in-plane phase diffraction pattern on the GISAXS may be a layer to which a thermal annealing is performed. In one embodiment, the layer for measuring the GISAXS is, for example, prepared by coating a coating solution, which is prepared by diluting the block copolymer in a solvent (for example, fluorobenzene) to a concentration of about 0.7 weight %, on a corresponding hydrophobic or hydrophilic surface so as for the coated layer to have a thickness of about 25 nm and an area of about 2.25 $cm^2$ (a width: 1.5 cm, a length: 1.5 cm) and then performed the thermal annealing thereto. The thermal annealing may be performed by maintaining the layer for about 1 hour at a temperature of 160° C. The GISAXS may be measured by irradiating the above prepared layer with X ray so as for an incident angle thereof to be in a range from 0.12 to 0.23 degrees. Diffraction patterns scattered from the layer may be obtained by a conventional measuring device (for example, 2D marCCD). Techniques confirming the existence of the in-plane phase diffraction pattern from the above obtained diffraction pattern is known in the field.

The block copolymer showing the above peaks in the GISAXS can show excellent self assembling property and the property can be effectively controlled according to an object.

The block copolymer may show at least one peak within a certain range of scattering vectors (the q values) when the X ray diffraction (XRD) analysis is performed.

In one embodiment, when the XRD is performed, the block copolymer may show at least one peak within a range from 0.5 $nm^{-1}$ to 10 $nm^{-1}$ of the scattering vectors (the q values). In other embodiment, the range of the scattering vectors (the q values) in which the at least one peak is observed may be from 0.7 $nm^{-1}$ or more, 0.9 $nm^{-1}$ or more, 1.1 $nm^{-1}$ or more, 1.3 $nm^{-1}$ or more or 1.5 $nm^{-1}$ or more. In other embodiment, the range of the scattering vectors (the q values) in which the at least one peak is observed may be from 9 $nm^{-1}$ or less, 8 $nm^{-1}$ or less, 7 $nm^{-1}$ or less, 6 $nm^{-1}$ or less, 5 $nm^{-1}$ or less, 4 $nm^{-1}$ or less, 3.5 $nm^{-1}$ or less or 3 $nm^{-1}$ or less.

The FWHM (full width at half maximum) of the peak observed within the above range of the scattering vectors (q) may be from 0.2 $nm^{-1}$ to 0.9 $nm^{-1}$. In another embodiment, the FWHM may be 0.25 $nm^{-1}$ or more, 0.3 $nm^{-1}$ or more or 0.4 $nm^{-1}$ or more. The FWHM may be, in another embodiment, 0.85 $nm^{-1}$ or less, 0.8 $nm^{-1}$ or less or 0.75 $nm^{-1}$ or less.

The term "FWHM (full width at half maximum)" as used herein may refer to a width (difference between scattering vectors (q's)) of a peak at a position showing an intensity half times as large as a maximum intensity.

In the XRD analysis, the scattering vector (q) and the FWHM are values by a numerical analysis, in which the least square technique is used, with respect to results of the XRD analysis described below. In the above method, the Gaussian fitting is performed with respect to a profile of peaks in the XRD pattern under a state where a position at which a XRD diffraction pattern has a lowest intensity becomes a baseline and the lowest intensity is converted to zero, and then the scattering vector (q) and the FWHM are obtained from the result of the Gaussian fitting. The R square of the Gaussian fitting is at least 0.9 or more, 0.92 or more, 0.94 or more or 0.96 or more. The method obtaining the above information from the XRD analysis is known, and, for example, a numerical value analysis program such as the origin may be used.

The block copolymer showing the peak having the above FWHM within the above range of scattering vectors (q's) may include a crystalline portion suitable for the self assembling. The block copolymer showing the peak having the above FWHM within the above range of scattering vectors (q's) may show an excellent self assembling property.

The XRD analysis may be performed by passing X-ray through a sample of the block copolymer and then measuring a scattering intensity according to scattering vector. The XRD analysis may be performed with respect to a block copolymer without any specific pre-treatment, and, for example, it may be performed by drying the block copolymer under an appropriate condition and then passing X ray through it. As the X ray, X ray, a vertical size of which is 0.023 mm and a horizontal size of which is 0.3 mm can be used. By using a measuring device (for example, 2D marCCD), a 2D diffraction pattern scattered from the sample is obtained as an image, and then the above fitting is performed with respect to the obtained diffraction pattern so as to obtain the scattering vector and the FWHM, and the like.

As described below, in case where at least one block of the block copolymer includes the chain, the number (n) of the chain-forming atoms and the scattering vector (q) obtained from the XRD analysis may satisfy the equation 1 below.

$$3\ nm^{-1} \sim 5\ nm^{-1} = nq/(2 \times \pi) \qquad [\text{Equation 1}]$$

In the Equation 1, the "n" is the number of the chain-forming atoms, and the "q" is the smallest scattering vector among scattering vectors at which peaks are observed in the XRD analysis or a scattering vector at which a peak having the largest area is observed. Further, the $\pi$ in the equation 1 is the ratio of the circumference of a circle to its diameter.

The scattering vectors and the like in the above equation 1 are values obtained in the same XRD analysis as described above.

The scattering value substituted with the value of the equation 1 may be a scattering value within a range from 0.5 $nm^{-1}$ to 10 $nm^{-1}$. In another embodiment, the scattering value substituted with the value of the equation 1 may be 0.7 $nm^{-1}$ or more, 0.9 $nm^{-1}$ or more, 1.1 $nm^{-1}$ or more, 1.3 $nm^{-1}$ or more or 1.5 $nm^{-1}$ or more. In another embodiment, the scattering value substituted with the value of the equation 1 may be 9 $nm^{-1}$ or less, 8 $nm^{-1}$ or less, 7 $nm^{-1}$ or less, 6 $nm^{-1}$ or less, 5 $nm^{-1}$ or less, 4 $nm^{-1}$ or less, 3.5 $nm^{-1}$ or less or 3 $nm^{-1}$ or less.

The equation 1 may represent a relation between the number of the chain-forming atoms and an interval (D) between blocks including the chains under a state where the block copolymer is self assembled and forms the phase separated structure. If the number of the chain-forming atoms of the block copolymer including the chains satisfies the equation 1, the crystallizability exhibited by the chain is improved, and therefore the phase separation property and the vertical aligning property may be largely improved. In another embodiment, the nq/(2×π) in the equation 1 may be 4.5 $nm^{-1}$ or less. In the above, the interval (D, unit: nm) between blocks including the chains can be calculated by a numerical formula, D=2×π/q. In the above, the "D" is the interval (D, unit: nm) between the blocks and the π and the q are the same as defined in the equation 1.

In one embodiment of the present application, an absolute value of a difference between surface energies of the first and the second blocks may be 10 mN/m or less, 9 mN/m or less, 8 mN/m or less, 7.5 mN/m or less or 7 mN/m or less. The absolute value of the difference between surface energies may be 1.5 mN/m or more, 2 mN/m or more or 2.5 mN/m or more. The structure in which the first and the second blocks, the absolute value of the difference between the surface energies of which is within the above range, are linked via the covalent bond may realize an effective microphase separation by a phase separation due to appropriate un-compatibilities. In the above, the first block may be the block having the chain as described above.

The surface energy may be measured by using a drop shape analyzer (DSA100 product manufactured in KRUSS, Co.). Specifically, the surface energy may be measured with respect to a layer prepared by coating a coating solution prepared by diluting a sample (a block copolymer or a homopolymer) to be measured in fluorobenzene to a solid content of about 2 weight % on a substrate so as for the coated layer to have a thickness of 50 nm and a coated area of 4 cm² (a width: 2 cm, a length: 2 cm); drying the coated layer for about an hour at the room temperature; and then performing a thermal annealing for about an hour at 160° C. On the layer after the thermal annealing is performed, deionized water of which the surface tension is known is dropped and then the contact angle is measured. The above process for obtaining the contact angle of the deionized water is repeated 5 times, and the average value of the 5 obtained contact angles are calculated. Identically, on the layer after the thermal annealing is performed, diiodomethane of which the surface tension is known is dropped and then the contact angle is measured. The above process for obtaining the contact angle of the diiodomethane is repeated 5 times, and the average value of the 5 obtained contact angles are calculated. After that, the surface energy may be obtained by substituting a value (Strom value) regarding the surface tension of the solvent through the Owens-Wendt-Rabel-Kaelble method using the obtained average values of the contact angles of the deionized water and the diiodomethane. The surface energy of each block in the block copolymer may be obtained by using the above described method with respect to a homopolymer prepared by monomers forming the corresponding block.

In case where the block copolymer comprises the above described chain, the block comprising the chain may have a larger surface energy than the other block. For example, if the first block comprises the chain, the first block may have a larger surface energy than the second block. In this case, the surface energy of the first block may be in a range from about 20 mN/m to about 40 mN/m. In another embodiment, the surface energy of the first block may be about 22 mN/m or more, about 24 mN/m or more, about 26 mN/m or more or about 28 mN/m or more. The surface energy of the first block may be about 38 mN/m or less, about 36 mN/m or less, about 34 mN/m or less or about 32 mN/m or less. Such a block copolymer including the above first block and showing the above difference between surface energies of blocks may show an excellent self assembling property.

In the block copolymer, an absolute value of a difference between densities of the first and the second blocks may be 0.25 g/cm³ or more, 0.3 g/cm³ or more, 0.35 g/cm³ or more, 0.4 g/cm³ or more or 0.45 g/cm³ or more. The absolute value of the difference between the densities may be 0.9 g/cm³ or less, 0.8 g/cm³ or less, 0.7 g/cm³ or less, 0.65 g/cm³ or less or 0.6 g/cm³ or less. The structure in which the first and the second blocks, the absolute value of the difference between the densities of which is within the above range, are linked via the covalent bond may realize an effective microphase separation by a phase separation due to appropriate un-compatibilities.

The density of each block in the block copolymer may be obtained through a known buoyancy method. For example, it may be obtained by analyzing a mass of a block copolymer in solvent such as ethanol, of which a mass and a density in the air are known.

In case where the block copolymer comprises the above described chain, the block comprising the chain may have a lower density than the other block. For example, if the first block comprises the chain, the first block may have a lower density than the second block. In this case, the density of the first block may be in a range from about 0.9 g/cm³ to about 1.5 g/cm³. In another embodiment, the density of the first block may be about 0.95 g/cm³ or more. The density of the first block may be about 1.4 g/cm³ or less, about 1.3 g/cm³ or less, about 1.2 g/cm³ or less, about 1.1 g/cm³ or less or about 1.05 g/cm³ or less. Such a block copolymer including the above first block and showing the above difference between the densities of blocks may show an excellent self assembling property. The surface energy and the density are measured at the room temperature.

The block copolymer may include a block, of which a volume fraction is from 0.4 to 0.8, and a block, of which a volume fraction is from 0.2 to 0.6. In case where the block copolymer comprises the chain, the block having the chain may have the volume fraction from 0.4 to 0.8. For example, the first block comprises the chain, the first block may have the volume fraction from 0.4 to 0.8 and the second block may have the volume fraction from 0.2 to 0.6. The sum of the volume fractions of the first and the second blocks may be 1. The block copolymer including each block in the above volume fractions may show an excellent self assembling property. The volume fraction of each block of the block copolymer may be obtained by using the density of each block and a molecular weight obtained by the Gel Permeation Chromatograph (GPC).

The block copolymer may have, for example, a number average molecular weight (Mn) in a range from approximately 3,000 to 300,000. The term "number average molecular weight" as used herein may refer to a converted value with respect to the standard polystyrene measured by the GPC (Gel Permeation Chromatography). Unless defined otherwise, the term "molecular weight" as used herein may refer to the number average molecular weight. The molecular weight (Mn), in another embodiment, may be, for example, 3000 or more, 5000 or more, 7000 or more, 9000 or more, 11000 or more, 13000 or more or 15000 or more. The molecular weight (Mn), in another embodiment, may be, for example, 250000 or less, 200000 or less, 180000 or less, 160000 or less, 140000 or less, 120000 or less, 100000 or less, 90000 or less, 80000 or less, 70000 or less, 60000 or less, 50000 or less, 40000 or less, 30000 or less, or 25000 or less. The block copolymer may have the polydispersity (Mw/Mn) in a range from 1.01 to 1.60. In another embodiment, the polydispersity may be about 1.1 or more, about 1.2 or more, about 1.3 or more, or about 1.4 or more.

In the above range, the block copolymer may exhibit an appropriate self assembling property. The number average molecular weight and the like of the block copolymer may be controlled considering the objected self assembled structure.

If the block copolymer at least includes the first and second blocks, a ratio of the first block, for example, the block including the chain in the block copolymer may be in a range of 10 mole % to 90 mole %.

The present application relates to a polymer layer including the block copolymer. The polymer layer may be used in various applications. For example, it can be used in a biosensor, a recording media such as a flash memory, a magnetic storage media or the pattern forming method or an electric device or an electronic device, and the like.

In one embodiment, the block copolymer in the polymer layer may be forming a periodic structure including a sphere, a cylinder, a gyroid, or a lamella by the self assembly.

For example, in one segment of the first block or the second block or other block linked to the above block via a covalent bond in the block copolymer, other segment may be forming the regular structure such as lamella form, cylinder form and the like.

The polymer layer may show the above in-plane phase diffraction pattern, i.e., the peak vertical to the X coordinate in the GISAXS diffraction pattern of the GISAXS analysis. In further embodiment, two or more peaks may be observed in the X coordinate of the GISAXS diffraction pattern. In case where two or more peaks are observed, the scattering vectors (the q values) may be confirmed with having constant ratios.

The present application relates also to a method for forming a polymer layer by using the block copolymer. The method may include forming a polymer layer including the block copolymer on a substrate in a self-assembled state. For example, the method may include forming a layer of the block copolymer or a coating solution in which the block copolymer is diluted in suitable solvent on the substrate by a coating and the like, and if necessary, then aging or heat-treating the layer.

The aging or the heat treatment may be performed based on, for example, a phase transition temperature or glass transition temperature of the block copolymer, and for example, may be performed at a temperature higher than the glass transition temperature or phase transition temperature. A time for the heat treatment is not particularly limited, and the heat treatment may be performed for approximately 1 minute to 72 hours, but may be changed if necessary. In addition, the temperature of the heat treatment of the polymer layer may be, for example, 100° C. to 250° C., but may be changed in consideration of the block copolymer used herein.

The formed layer may be aged in a non-polar solvent and/or a polar solvent at the room temperature for approximately 1 minute to 72 hours.

The present application relates also to a pattern-forming method. The method may include selectively removing the first or second block of the block copolymer from a laminate comprising a substrate and a polymer layer that is formed on a surface of the substrate and that includes a self-assembled block copolymer. The method may be a method for forming a pattern on the above substrate. For example, the method may include forming the polymer layer on the substrate, selectively removing one block or two or more blocks of the block copolymer that is in the polymer layer; and then etching the substrate. By the above method, for example, nano-scaled micropattern may be formed. Further, according to shapes of the block copolymer in the polymer layer, various shapes of pattern such as nano-rod or nano-hole can be formed by the above method. If necessary, in order to form a pattern, the block copolymer may be mixed with another copolymer or homopolymer. A kind of the substrate applied to this method may be selected without particular limitation, and, for example, silicon oxide and the like may be applied.

For example, according to the method, a nano-scale pattern of silicon oxide having a high aspect ratio may be formed. For example, various types of patterns such as a nanorod or nanohole pattern may be formed by forming the polymer layer on the silicon oxide, selectively removing any one block of the block copolymer in a state where the block copolymer in the polymer layer is formed in a predetermined structure, and etching the silicon oxide in various methods, for example, reactive ion etching. In addition, according to the above method, a nano pattern having a high aspect ratio can be formed.

For example, the pattern may be formed to a scale of several tens of nanometers, and such a pattern may be applied in various uses including a next-generation information electronic magnetic recording medium.

For example, a pattern in which nano structures, for example, nanowires, having a width of approximately 3 to 40 nm are disposed at an interval of approximately 6 to 80 nm may be formed by the above-described method. In another embodiment, a structure in which nanoholes having a width, for example, a diameter of approximately 3 to 40 nm are disposed at an interval of approximately 6 to 80 nm can be implemented.

In addition, in this structure, nanowires or nanoholes may be formed to have a high aspect ratio.

In this method, a method of selectively removing any one block of the block copolymer is not particularly limited, and for example, a method of removing a relatively soft block by irradiating a suitable electromagnetic wave, for example, ultra violet rays to a polymer layer may be used. In this case, conditions for ultra violet radiation may be determined according to a type of the block of the block copolymer, and ultra violet rays having a wavelength of approximately 254 nm may be irradiated for 1 to 60 minutes.

In addition, followed by the ultra violet radiation, the polymer layer may be treated with an acid to further remove a segment degraded by the ultra violet rays.

In addition, the etching of the substrate using the polymer layer from which a block is selectively removed may be performed by reactive ion etching using $CF_4/Ar$ ions, and followed by the above process, and removing the polymer layer from the substrate by oxygen plasma treatment may be further performed.

EFFECTS

Figure 1:
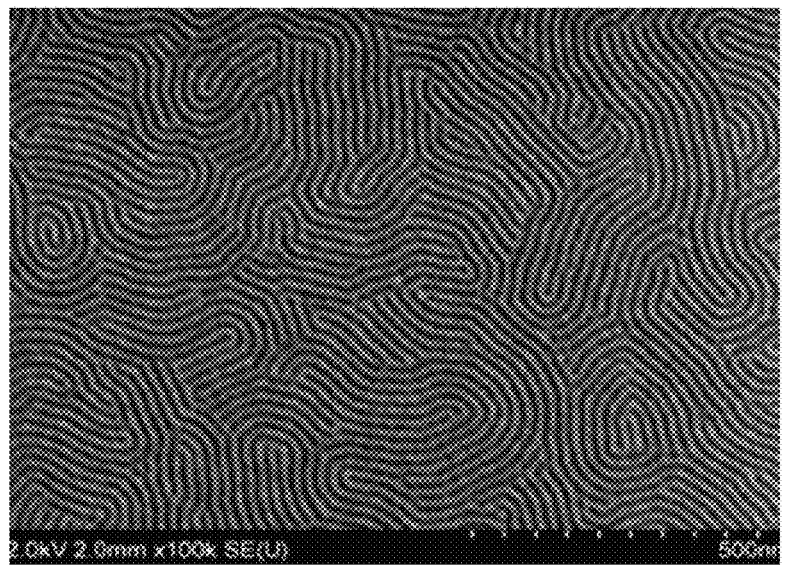
FIGS. 1 to 15 are SEM or AFM images of polymer layers and show results of GISAXS analysis on polymer layers.
Figure 2:
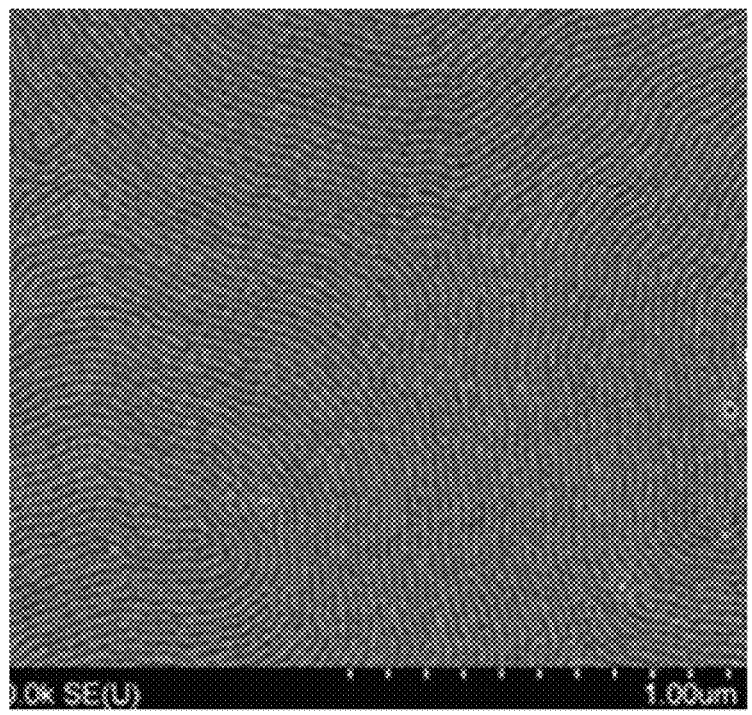
Figure 3:
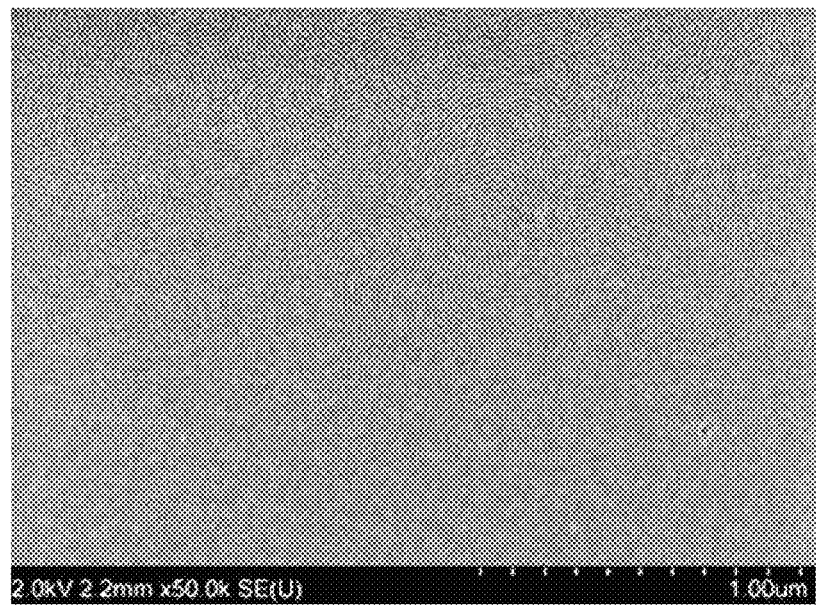
Figure 4:
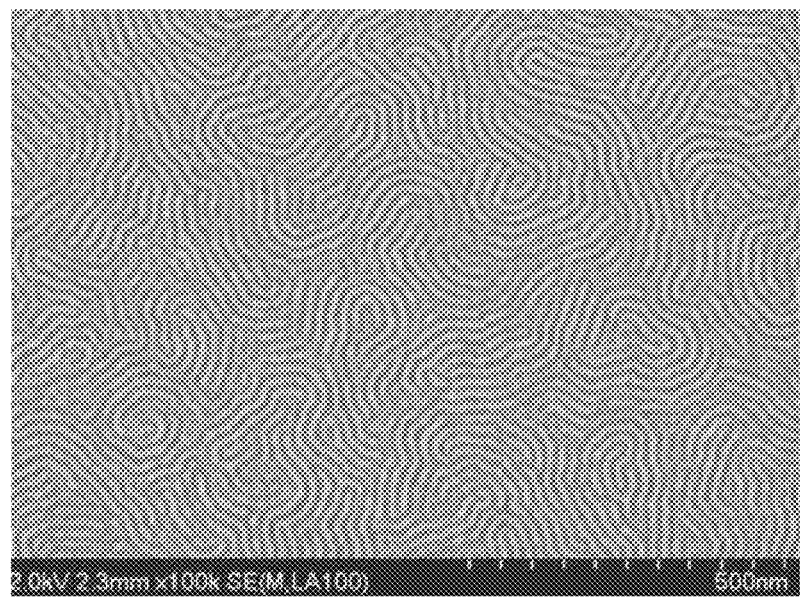
Figure 5:
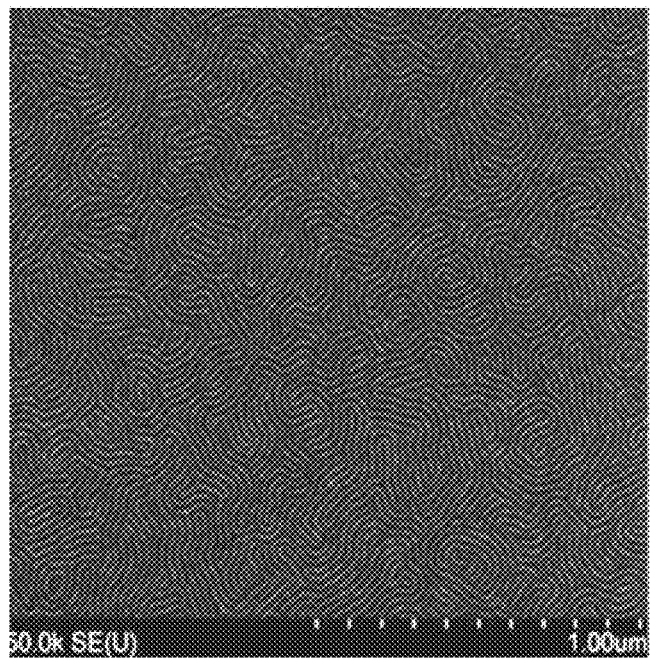
Figure 6:
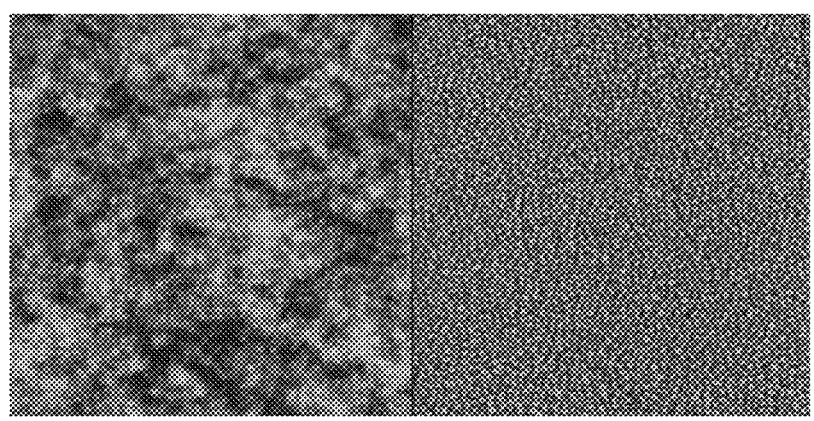
Figure 7:
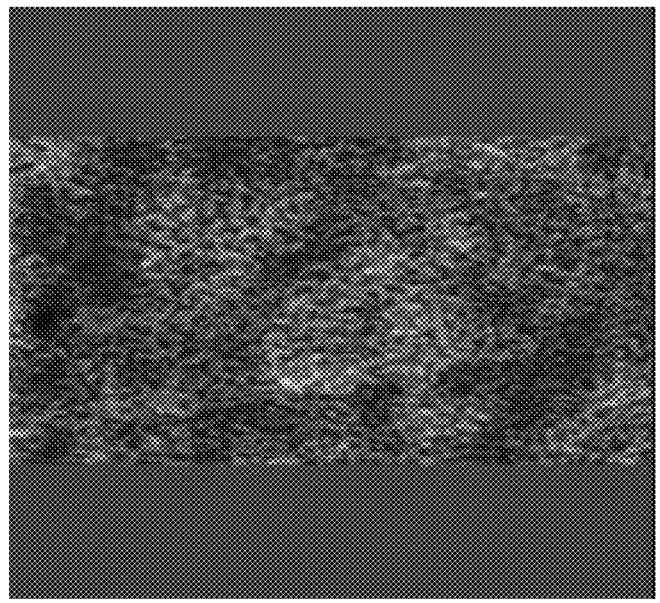
Figure 8:
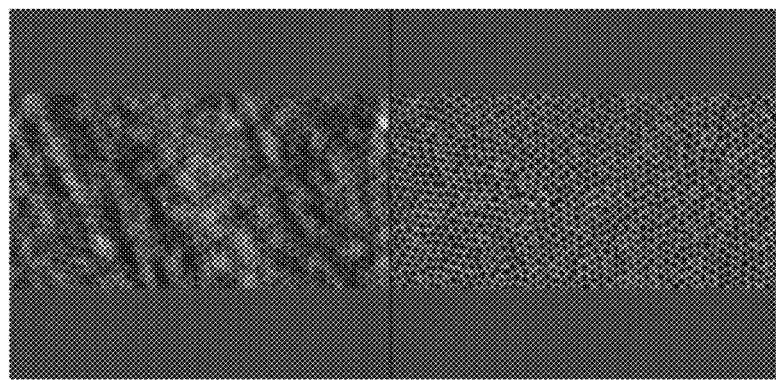
Figure 9:
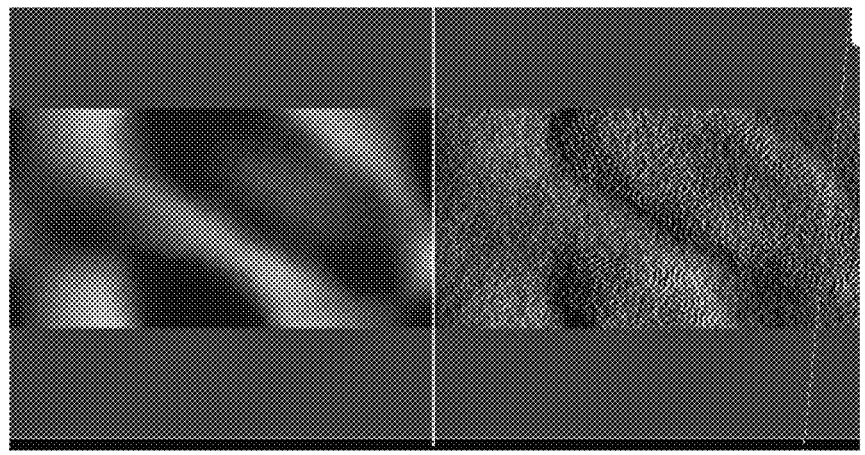
Figure 10:
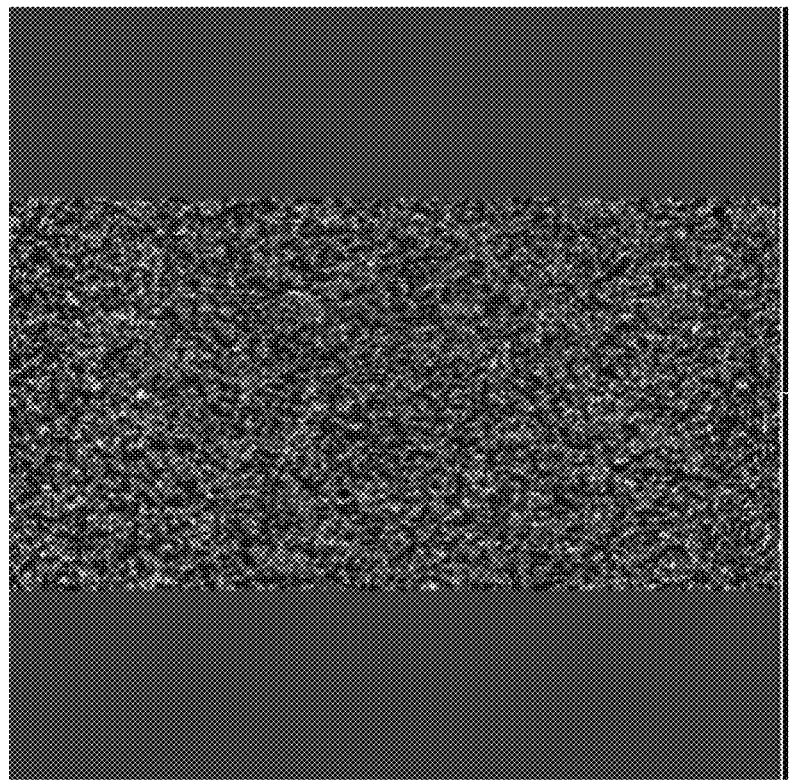
Figure 11:
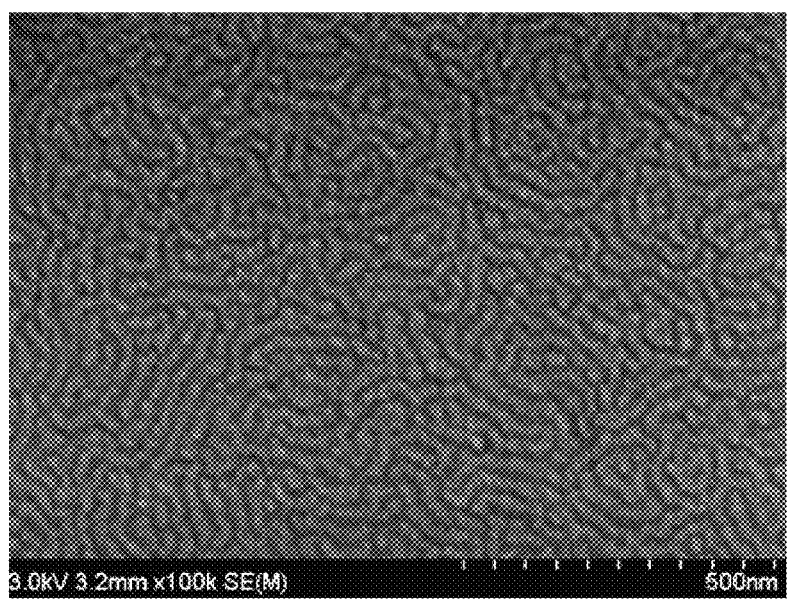
Figure 12:
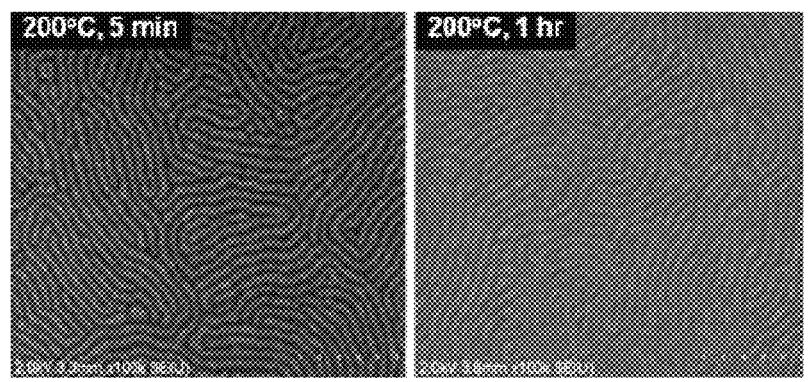
Figure 13:
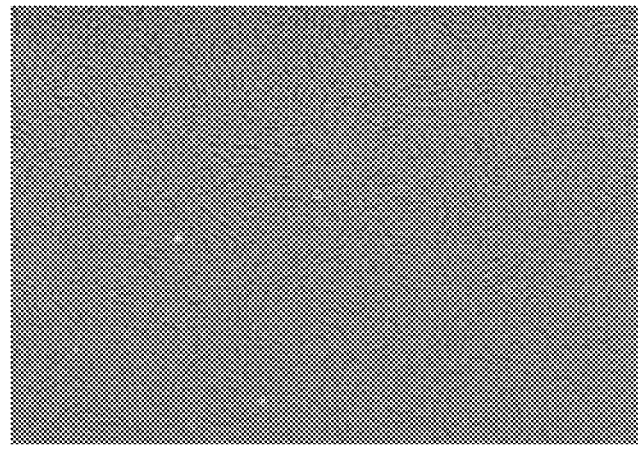

The present application may provide the block copolymers and their application. The block copolymer has an excellent self assembling property and phase separation and various required functions can be freely imparted thereto as necessary.

ILLUSTRATIVE EMBODIMENTS

Hereinafter, the present application will be described in detail with reference to Examples and Comparative Examples, but the scope of the present application is not limited to the following examples.

1. NMR Analysis

The NMR analysis was performed at the room temperature by using a NMR spectrometer including a Varian Unity Inova (500 MHz) spectrometer having a triple resonance 5 mm probe. A sample to be analyzed was used after diluting it in solvent (CDCl$_3$) for the NMR analysis to a concentration of approximately 10 mg/ml and a chemical shift (δ) was expressed in ppm.

Abbreviation br=wide signal, s=singlet, d=doublet, dd=double doublet, t=triplet, dt=double triplet, q=quadruplet, p=quintuplet, m=multiplet 2. GPC (Gel Permeation Chromatograph)

The number average molecular weight and the polydispersity were measured by the GPC (Gel Permeation Chromatograph). In a 5 mL vial, a block copolymer or a macroinitiator to be measured of Example or Comparative Example and then diluted to a concentration of about 1 mg/mL. Then, the standard sample for a calibration and a sample to be analyzed were filtered by a syringe filter (pore size: 0.45 μm) and then analyzed. ChemStation from the Agilent technologies, Co. was used as an analysis program. The number average molecular weight (Mn) and the weight average molecular weight (Mw) were obtained by comparing an elution time of the sample with a calibration curve and then the polydispersity (PDI) was obtained from their ratio (Mw/Mn). The measuring condition of the GPC was as below.

<GPC Measuring Condition>

Device: a 1200 series from Agilent technologies, Co.

Column: two of PLgel mixed B from Polymer laboratories, Co. were used

Solvent: THF

Temperature of the column: 35° C.

Concentration of Sample: 1 mg/mL, 200 L injection

Standard Sample: Polystyrene (Mp: 3900000, 723000, 316500, 52200, 31400, 7200, 3940, 485)

Preparation Example 1

A compound (DPM-C12) of the Formula A below was synthesized by the below method. To a 250 mL flask, hydroquinone (10.0 g, 94.2 mmole) and 1-bromododecane (23.5 g, 94.2 mmole) were added and dissolved in 100 mL acetonitrile, an excessive amount of potassium carbonate was added thereto and then the mixture was reacted at 75° C. for approximately 48 hours under nitrogen. After the reaction, remaining potassium carbonate and acetonitrile used for the reaction were removed. The work up was performed by adding a mixed solvent of dichloromethane (DCM) and water, and separated organic layers were collected and dehydrated through MgSO$_4$. Subsequently, a white solid intermediate was obtained with a yield of approximately 37% using DCM through column chromatography.

<NMR Analysis Result of the Intermediate>

$^1$H-NMR (CDCl$_3$): δ6.77 (dd, 4H); 54.45 (s, 1H); δ3.89 (t, 2H); δ1.75 (p, 2H); δ1.43 (p, 2H); δ1.33-1.26 (m, 16H); δ0.88 (t, 3H)

The synthesized intermediate (9.8 g, 35.2 mmole), methacrylic acid (6.0 g, 69.7 mmole), dicyclohexylcarbodiimide (DCC; 10.8 g, 52.3 mmole) and p-dimethylaminopyridine (DMPA; 1.7 g, 13.9 mmol) were put into a flask, 120 ml of methylenechloride was added, and a reaction was performed at the room temperature for 24 hours under nitrogen. After the reaction was completed, a urea salt produced in the reaction was removed through a filter, and remaining methylenechloride was also removed. Impurities were removed using hexane and DCM (dichloromethane) as mobile phases though column chromatography, and the obtained product was recrystallized in a mixed solvent of methanol and water (mixed in 1:1 weight ratio), thereby obtaining a white solid product (DPM-C12)(7.7 g, 22.2 mmol) with a yield of 63%.

<NMR Analysis Result with Respect to DPM-C12>

$^1$H-NMR (CDCl$_3$): δ7.02 (dd, 2H); δ6.89 (dd, 2H); δ6.32 (dt, 1H); δ5.73 (dt, 1H); δ3.94 (1, 2H); δ2.05 (dd, 3H); δ1.76 (p, 2H); δ1.43 (p, 2H); 1.34-1.27 (m, 16H); δ0.88 (1, 3H)

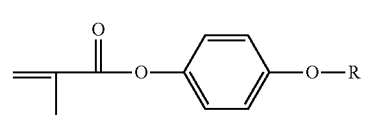

[Formula A]

In the above, the R is a linear alkyl having 12 carbon atoms.

Preparation Example 2

A compound (DPM-C8) of the Formula B below was synthesized according to the method of Preparation Example 1, except that 1-bromooctane was used instead of the 1-bromododecane. The NMR analysis result with respect to the above compound is as below.

<NMR Analysis Result with Respect to DPM-C8>

$^1$H-NMR (CDCl$_3$): δ7.02 (dd, 2H); δ6.89 (dd, 2H); δ6.32 (dt, 1H); δ5.73 (dt, 1H); δ3.94 (1, 2H); δ2.05 (dd, 3H); δ1.76 (p, 2H); δ1.45 (p, 2H); 1.33-1.29 (m, 8H); δ0.89 (1, 3H)

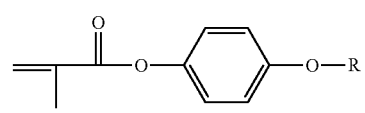

[Formula B]

In the above, the R is a linear alkyl having 8 carbon atoms.

Preparation Example 3

A compound (DPM-C10) of the Formula C below was synthesized according to the method of Preparation Example 1, except that 1-bromodecane was used instead of the 1-bromododecane. The NMR analysis result with respect to the above compound is as below.

<NMR Analysis Result with Respect to DPM-C10>

$^1$H-NMR (CDCl$_3$): δ7.02 (dd, 2H); δ6.89 (dd, 2H); δ6.33 (dt, 1H); δ5.72 (dt, 1H); δ3.94 (t, 2H); δ2.06 (dd, 3H); δ1.77 (p, 2H); δ1.45 (p, 2H); 1.34-1.28 (m, 12H); δ0.89 (t, 3H)

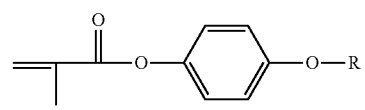

[Formula C]

In the above, the R is a linear alkyl having 10 carbon atoms.

Preparation Example 4

A compound (DPM-C14) of the Formula D below was synthesized according to the method of Preparation Example 1, except that 1-bromotetradecane was used instead of the 1-bromododecane. The NMR analysis result with respect to the above compound is as below.

<NMR Analysis Result with Respect to DPM-C14>
$^1$H-NMR (CDCl$_3$): δ7.02 (dd, 2H); δ6.89 (dd, 2H); δ6.33 (dt, 1H); δ5.73 (dt, 1H); δ3.94 (t, 2H); δ2.05 (dd, 3H); δ1.77 (p, 2H); δ1.45 (p, 2H); 1.36-1.27 (m, 20H); δ0.88 (t, 3H.)

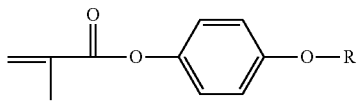
[Formula D]

In the above, the R is a linear alkyl having 14 carbon atoms.

Preparation Example 5

A compound (DPM-C16) of the Formula E below was synthesized according to the method of Preparation Example 1, except that 1-bromohexadecane was used instead of the 1-bromododecane. The NMR analysis result with respect to the above compound is as below.

<NMR Analysis Result with Respect to DPM-C16>
$^1$H-NMR (CDCl$_3$): δ7.01 (dd, 2H); δ6.88 (dd, 2H); δ6.32 (dt, 1H); δ5.73 (dt, 1H); δ3.94 (1, 2H); δ2.05 (dd, 3H); δ1.77 (p, 2H); δ1.45 (p, 2H); 1.36-1.26 (m, 24H); δ0.89 (1, 3H)

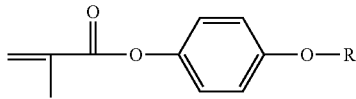
[Formula E]

In the above, the R is a linear alkyl having 16 carbon atoms.

Preparation Example 6

A compound (DPM-N2) of the Formula F below was synthesized by the below method. To a 500 mL flask, Pd/C (palladium on carbon) (1.13 g, 1.06 mmole) and 200 mL of 2-propanol were added and then ammonium formate dissolved in 20 mL of water was added, and then the Pd/C was activated by performing a reaction at the room temperature for 1 minute. Then, 4-aminophenol (1.15 g, 10.6 mmole) and lauric aldehyde (1.95 g, 10.6 mmole) were added thereto and the mixture was reacted at the room temperature for 1 minute by stirring it under nitrogen. After the reaction, the Pd/C was removed and the 2-propanol used for the reaction was removed, and then the mixture was extracted by water and methylene chloride so as to remove unreacted products. An organic layer was collected and dehydrated through MgSO$_4$. A crude product was purified by a column chromatography (mobile phase: hexane/ethyl acetate) and thereby a colorless solid intermediate (1.98 g, 7.1 mmole) was obtained (yield: 67 weight %).

<NMR Analysis Result of the Intermediate>
$^1$H-NMR (DMSO-d): δ6.69 (dd, 2H); δ6.53 (dd, 2H); δ3.05 (t, 2H); δ1.59 (p, 2H); δ1.40-1.26 (m, 16H); δ0.88 (t, 3H)

The synthesized intermediate (1.98 g, 7.1 mmole), methacrylic acid (0.92 g, 10.7 mmole), dicyclohexylcarbodiimide (DCC; 2.21 g, 10.7 mmole) and p-dimethylaminopyridine (DMPA; 0.35 g, 2.8 mmol) were put into a flask, 100 ml of methylenechloride was added, and a reaction was performed at the room temperature for 24 hours under nitrogen. After the reaction was completed, a urea salt produced during the reaction was removed through a filter, and remaining methylenechloride was also removed. Impurities were removed using hexane and DCM (dichloromethane) as mobile phases though column chromatography, and the obtained product was recrystallized in a mixed solvent (methanol:water=3:1 (weight ratio)) of methanol and water, thereby obtaining a white solid product (DPM-N2)(1.94 g, 5.6 mmole) with a yield of 79%.

<NMR Analysis Result with Respect to DPM-N2>
$^1$H-NMR (CDCl$_3$): δ6.92 (dd, 2H); δ6.58 (dd, 2H); δ6.31 (dt, 1H); δ5.70 (dt, 1H); δ3.60 (s, 1H); δ3.08 (t, 2H); δ2.05 (dd, 3H); δ1.61 (p, 2H); δ1.30-1.27 (m, 16H); δ0.88 (t, 3H)

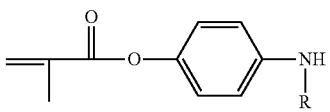
[Formula F]

In the above, the R is a linear alkyl having 12 carbon atoms.

Preparation Example 7

A compound (DPM-C4) of the Formula G below was synthesized according to the method of Preparation Example 1, except that 1-bromobutane was used instead of the 1-bromododecane. The NMR analysis result with respect to the above compound is as below.

<NMR Analysis Result with Respect to DPM-C4>
$^1$H-NMR (CDCl$_3$): δ7.02 (dd, 2H); δ6.89 (dd, 2H); δ6.33 (dt, 1H); δ5.73 (dt, 1H); δ3.95 (t, 2H); δ2.06 (dd, 3H); δ1.76 (p, 2H); δ1.49 (p, 2H); δ0.98 (t, 3H)

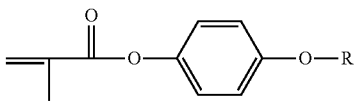
[Formula G]

In the above, the R is a linear alkyl having 4 carbon atoms.

Example 1

2.0 g of the compound (DPM-C12) of Preparation Example 1, 64 mg of RAFT (Reversible Addition-Fragmentation chain transfer) reagent (cyanoisopropyl dithiobenzoate), 23 mg of AIBN (azobisisobutyronitrile) and 5.34 mL of benzene were added to a 10 mL flask and then were stirred at the room temperature for 30 minutes and then the RAFT (reversible addition fragmentation chain transfer) polymerization was performed at 70° C. for 4 hours. After the polymerization, the reacted solution was precipitated in 250 mL of methanol that was an extraction solvent, was vacuum filtered and dried so as to obtain pink macroinitiator. The yield of the macroinitiator was about 86%, and its number average molecular weight (Mn) and polydispersity (Mw/Mn) were 9,000 and 1.16, respectively.

0.3 g of the macroinitiator, 2.7174 g of pentafluorostyrene and 1.306 mL of benzene were added to a 10 mL Schlenk flask and then were stirred at the room temperature for 30 minutes and then the RAFT (reversible addition fragmentation chain transfer) polymerization was performed at 115° C. for 4 hours. After the polymerization, the reacted solution was precipitated in 250 mL of methanol that was an extraction solvent, was vacuum filtered and dried so as to obtain light pink block copolymer. The yield of the block copolymer was about 18%, and its number average molecular weight (Mn) and polydispersity (Mw/Mn) were 16,300 and 1.13, respectively. The block copolymer includes the first block derived from the compound (DPM-C12) of Preparation Example 1 and the second block derived from the pentafluorostyrene.

Example 2

A block copolymer was prepared by the same method as in Example 1 except that a macroinitiator prepared by using the compound (DPM-C8) of Preparation Example 2 instead of the compound (DPM-C12) of Preparation Example 1 and pentafluorostyrene were used. The block copolymer includes the first block derived from the compound (DPM-C8) of Preparation Example 2 and the second block derived from the pentafluorostyrene.

Example 3

A block copolymer was prepared by the same method as in Example 1 except that a macroinitiator prepared by using the compound (DPM-C10) of Preparation Example 3 instead of the compound (DPM-C12) of Preparation Example 1 and pentafluorostyrene were used. The block copolymer includes the first block derived from the compound (DPM-C10) of Preparation Example 3 and the second block derived from the pentafluorostyrene.

Example 4

A block copolymer was prepared by the same method as in Example 1 except that a macroinitiator prepared by using the compound (DPM-C14) of Preparation Example 4 instead of the compound (DPM-C12) of Preparation Example 1 and pentafluorostyrene were used. The block copolymer includes the first block derived from the compound (DPM-C14) of Preparation Example 4 and the second block derived from the pentafluorostyrene.

Example 5

A block copolymer was prepared by the same method as in Example 1 except that a macroinitiator prepared by using the compound (DPM-C16) of Preparation Example 5 instead of the compound (DPM-C12) of Preparation Example 1 and pentafluorostyrene were used. The block copolymer includes the first block derived from the compound (DPM-C16) of Preparation Example 5 and the second block derived from the pentafluorostyrene.

Example 6

Synthesis of a Monomer

3-Hydroxy-1,2,4,5-tetrafluorostyrene was synthesized according to the below method. Pentafluorostyrene (25 g, 129 mmole) was added to a mixed solution of 400 mL of tert-butanol and potassium hydroxide (37.5 g, 161 mmole); and then was subjected to a reflux reaction for 2 hours. The product after the reaction was cooled to the room temperature, 1200 mL of water was added and the remaining butanol used for the reaction was volatilized. The adduct was extracted 3 times by diethyl ether (300 mL), an aqueous layer was acidified by 10 weight % of hydrochloric acid solution until its pH became 3, and thereby target product was precipitated. Precipitated product was extracted 3 times by diethyl ether (300 mL) and an organic layer was collected. The organic layer was dehydrated by $MgSO_4$ and solvent was removed. Crude product was purified in a column chromatograph by using hexane and DCM (dichloromethane) as mobile phase and thereby colorless liquid 3-hydroxy-1,2,4,5-tetrafluorostyrene (11.4 g) was obtained. Its NMR analysis result is as below.

<NMR Analysis Result>
$^1$H-NMR (DMSO-d): δ11.7 (s, 1H); δ6.60 (dd, 1H); δ5.89 (d, 1H); δ5.62 (d, 1H)

Synthesis of a Block Copolymer

In benzene, AIBN (azobisisobutyronitrile), RAFT (reversible addition fragmentation chain transfer) reagent (2-cyano-2-propyl dodecyl trithiocarbonate) and the compound (DPM-C12) of Preparation Example 1 were dissolved in a weight ratio of 50:1:0.2 (DPM-C12:RAFT reagent:AIBN) (Concentration: 70 weight %), and then a macroinitiator (a number average molecular weight: 14000, polydispersity: 1.2) was prepared by reacting the mixture for 4 hours at 70° C. under nitrogen. Then, in benzene, the synthesized macroinitiator, 3-hydroxy-1,2,4,5-tetrafluorostyrene (TFS-OH) and AIBN (azobisisobutyronitrile) were dissolved in a weight ratio of 1:200:0.5 (the macroinitiator:TFS-OH:AIBN) (Concentration: 30 weight %), and then a block copolymer (a number average molecular weight: 35000, polydispersity: 1.2) was prepared by reacting the mixture for 6 hours at 70° C. under nitrogen. The block copolymer includes the first block derived from the compound of Preparation Example 1 and the second block derived from the 3-hydroxy-1,2,4,5-tetrafluorostyrene.

Example 7

Synthesis of a Monomer

The compound of the Formula H below was synthesized according to the below method. Phthalimide (10.0 g, 54 mmole) and chloromethylstyrene (8.2 g, 54 mmole) were added to 50 mL of DMF (dimethyl formamide) and then were reacted for 18 hours at 55° C. under nitrogen. After the reaction, 100 mL of ethyl acetate and 100 mL of distilled water were added to the reacted product, and then an organic layer was collected and then washed by brine solution. Collected organic layer was treated by $MgSO_4$ and thereby water was removed and then solvent was finally removed and then re-crystallized by pentane so as to obtain white solid target compound (11.1 g). Its NMR analysis result is as below.

<NMR Analysis Result>
$^1$H-NMR (CDCl$_3$): δ7.84 (dd, 2H); δ7.70 (dd, 2H); δ7.40-7.34 (m, 4H); δ6.67 (dd, 1H); δ5.71 (d, 1H); δ5.22 (d, 1H); δ4.83 (s, 2H)

[Formula H]

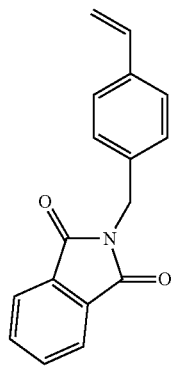

Synthesis of a Block Copolymer

In benzene, AIBN (azobisisobutyronitrile), RAFT (reversible addition fragmentation chain transfer) reagent (2-cyano-2-propyl dodecyl trithiocarbonate) and the compound (DPM-C12) of Preparation Example 1 were dissolved in a weight ratio of 50:1:0.2 (DPM-C12:RAFT reagent: AIBN) (Concentration: 70 weight %), and then a macroinitiator (a number average molecular weight: 14000, polydispersity: 1.2) was prepared by reacting the mixture for 4 hours at 70° C. under nitrogen. Then, in benzene, the synthesized macroinitiator, the compound (TFS-PhIM) of Formula H and AIBN (azobisisobutyronitrile) were dissolved in a weight ratio of 1:200:0.5 (the macroinitiator: TFS-PhIM:AIBN) (Concentration: 30 weight %), and then a block copolymer (a number average molecular weight: 35000, polydispersity: 1.2) was prepared by reacting the mixture for 6 hours at 70° C. under nitrogen. The block copolymer includes the first block derived from the compound of Example 1 and the second block derived from the compound of Formula H.

Example 8

In a 10 mL flask (Schlenk flask), 0.8662 g of the compound (DPM-C12) of the Preparation Example 1, 0.5 g of a macroinitiator (Macro-PEO)(poly(ethylene glycol)-4-cyano-4-(phenylcarbonothioylthio)pentanoate, a weight average molecular weight (Mw): 10,000, Sigma Aldrich) to the both end portions of which RAFT (Reversible Addition-Fragmentation chain Transfer) reagents were linked, 4.1 mg of AIBN (azobisisobutyronitrile) and 3.9 mL of anisole were added and then were stirred at the room temperature under a nitrogen for 30 minutes and then the RAFT (Reversible Addition-Fragmentation chain Transfer) polymerization was performed for 12 hours in a silicone oil container of 70° C. After the polymerization, the reacted solution was precipitated in 250 mL of methanol that is an extraction solvent, and then was subjected to a vacuum filtration and dried, a pale pink block copolymer (Yield: 30.5%, a number average molecular weight (Mn): 34300, polydispersity (Mw/Mn): 1.60) was obtained. The block copolymer includes the first block derived from the compound of Preparation Example 1 and the second block of the polyethyleneoxide.

Example 9

In a 10 mL flask (Schlenk flask), 2.0 g of the compound (DPM-C12) of the Preparation Example 1, 25.5 mg of RAFT (Reversible Addition-Fragmentation chain Transfer) reagents (cyanoisopropyl dithiobenzoate), 9.4 mg of AIBN (azobisisobutyronitrile) and 5.34 mL of benzene were added and then were stirred at the room temperature under a nitrogen for 30 minutes and then the RAFT (Reversible Addition-Fragmentation chain Transfer) polymerization was performed for 4 hours in a silicone oil container of 70° C. After the polymerization, the reacted solution was precipitated in 250 mL of methanol that is an extraction solvent, and then was subjected to a vacuum filtration and dried, a pink macroinitiator to both ends of which the RAFT (Reversible Addition-Fragmentation chain Transfer) reagents were linked was obtained. The yield, a number average molecular weight (Mn) and polydispersity (Mw/Mn) of the macroinitiator were 81.6 weight %, 15400 and 1.16 respectively. In a 10 mL flask (Schlenk flask), 1.177 g of styrene, 0.3 g of the macroinitiator and 0.449 mL of benzene were added and then were stirred at the room temperature under a nitrogen for 30 minutes and then the RAFT (Reversible Addition-Fragmentation chain Transfer) polymerization was performed for 4 hours in a silicone oil container of 115° C. After the polymerization, the reacted solution was precipitated in 250 mL of methanol that is an extraction solvent, and then was subjected to a vacuum filtration and dried, a pale pink novel block copolymer was prepared. The yield, a number average molecular weight (Mn) and polydispersity (Mw/Mn) of the block copolymer were 39.3 weight %, 31800 and 1.25 respectively. The block copolymer includes the first block derived from the compound of Preparation Example 1 and the second block of the polystyrene.

Example 10

In a 10 mL flask (Schlenk flask), 0.33 g of the macroinitiator prepared in Example 9, 1.889 g of 4-trimethylsilylstyrene, 2.3 mg of AIBN (azobisisobutyronitrile) and 6.484 mL of benzene were added and then were stirred at the room temperature under a nitrogen for 30 minutes and then the RAFT (Reversible Addition-Fragmentation chain Transfer) polymerization was performed for 24 hours in a silicone oil container of 70° C. After the polymerization, the reacted solution was precipitated in 250 mL of methanol that is an extraction solvent, and then was subjected to a vacuum filtration and dried, a pale pink novel block copolymer was prepared. The yield, a number average molecular weight (Mn) and polydispersity (Mw/Mn) of the block copolymer were 44.2 weight %, 29600 and 1.35 respectively. The block copolymer includes the first block derived from the compound of Preparation Example 1 and the second block of the poly(4-trimethylsilylstyrene).

Example 11

Synthesis of a Monomer

The compound of the Formula I below was synthesized according to the below method. Pentafluorostyrene (25 g, 129 mmole) was added to a mixed solution of 400 mL of tert-butanol and potassium hydroxide (37.5 g, 161 mmole); and then was subjected to a reflux reaction for 2 hours. The product after the reaction was cooled to the room temperature, 1200 mL of water was added and the remaining butanol used for the reaction was volatilized. The adduct was extracted 3 times by diethyl ether (300 mL), an aqueous layer was acidified by 10 weight % of hydrochloric acid solution until its pH became 3, and thereby target product was precipitated. Precipitated product was extracted 3 times by diethyl ether (300 mL) and an organic layer was collected. The organic layer was dehydrated by $MgSO_4$ and solvent was removed. Crude product was purified in a column chromatograph by using hexane and DCM (dichloromethane) as mobile phase and thereby a colorless liquid intermediate (3-hydroxy-1,2,4,5-tetrafluorostyrene) (11.4 g) was obtained. Its NMR analysis result is as below.

<NMR Analysis Result>

$^1$H-NMR (DMSO-d): δ11.7 (s, 1H); δ6.60 (dd, 1H); δ5.89 (d, 1H); δ5.62 (d, 1H)

The intermediate (11.4 g, 59 mmole) was dissolved in DCM (dichloromethane) (250 mL) and then imidazole (8.0 g, 118 mmole), DMPA (p-dimethylaminopyridine (0.29 g, 2.4 mmole) and tert-butylchlorodimethylsilane (17.8 g, 118 mmole) were added thereto. The mixture was reacted by stirring it at the room temperature for 24 hours and the reaction was terminated by adding 100 mL of brine and then additional extraction was performed by DCM. A collected organic layer of DCM was dehydrated by $MgSO_4$ and solvent was removed so as to obtain crude product. Colorless liquid target product (10.5 g) was obtained after purification in a column chromatograph by using hexane and DCM as mobile phase. NMR result of the target product is as below.

<NMR Analysis Result>
$^1$H-NMR (CDCl$_3$): δ6.62 (dd, 1H); δ6.01 (d, 1H); δ5.59 (d, 1H); δ1.02 (t, 9H); δ0.23 (t, 6H)

[Formula I]

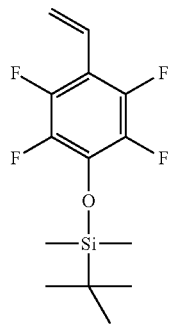

Synthesis of a Block Copolymer

In benzene, AIBN (azobisisobutyronitrile), RAFT (reversible addition fragmentation chain transfer) reagent (2-cyano-2-propyl dodecyl trithiocarbonate) and the compound (DPM-C12) of Preparation Example 1 were dissolved in a weight ratio of 50:1:0.2 (DPM-C12:RAFT reagent: AIBN) (Concentration: 70 weight %), and then a macroinitiator (a number average molecular weight: 14000, polydispersity: 1.2) was prepared by reacting the mixture for 4 hours at 70° C. under nitrogen. Then, in benzene, the synthesized macroinitiator, the compound (TFS-S) of Formula I and AIBN (azobisisobutyronitrile) were dissolved in a weight ratio of 1:200:0.5 (the macroinitiator:TFS-S:AIBN) (Concentration: 30 weight %), and then a block copolymer (a number average molecular weight: 35000, polydispersity: 1.2) was prepared by reacting the mixture for 6 hours at 70° C. under nitrogen. The block copolymer includes the first block derived from the compound of Preparation Example 1 and the second block derived from the compound of Formula I.

Example 12

In benzene, AIBN (azobisisobutyronitrile), RAFT (reversible addition fragmentation chain transfer) reagent (2-cyano-2-propyl dodecyl trithiocarbonate) and the compound (DPM-N1) of Preparation Example 6 were dissolved in a weight ratio of 26:1:0.5 (DPM-C12:RAFT reagent: AIBN) (Concentration: 70 weight %), and then a macroinitiator (a number average molecular weight: 9700, polydispersity: 1.2) was prepared by reacting the mixture for 4 hours at 70° C. under nitrogen. Then, in benzene, the synthesized macroinitiator, pentafluorostyrene (PFS) and AIBN (azobisisobutyronitrile) were dissolved in a weight ratio of 1:600:0.5 (the macroinitiator:PFS:AIBN) (Concentration: 30 weight %), and then a block copolymer (a number average molecular weight: 17300, polydispersity: 1.2) was prepared by reacting the mixture for 6 hours at 115° C. under nitrogen. The block copolymer includes the first block derived from the compound of Preparation Example 6 and the second block derived from the pentafluorostyrene.

Example 13

A block copolymer was prepared by the same method as in Example 1 except that a macroinitiator prepared by using the compound (DPM-C4) of Preparation Example 7 instead of the compound (DPM-C12) of Preparation Example 1 and pentafluorostyrene were used. The block copolymer includes the first block derived from the compound (DPM-C4) of Preparation Example 7 and the second block derived from the pentafluorostyrene.

Comparative Example 1

A block copolymer was prepared by the same method as in Example 1 except that a macroinitiator prepared by using 4-methoxyphenyl methacrylate instead of the compound (DPM-C12) of Preparation Example 1 and pentafluorostyrene were used. The block copolymer includes the first block derived from the 4-methoxyphenyl methacrylate and the second block derived from the pentafluorostyrene.

Comparative Example 2

A block copolymer was prepared by the same method as in Example 1 except that a macroinitiator prepared by using dodecyl methacrylate instead of the compound (DPM-C12) of Preparation Example 1 and pentafluorostyrene were used. The block copolymer includes the first block derived from the dodecyl methacrylate and the second block derived from the pentafluorostyrene.

Test Example 1

Figure 14:
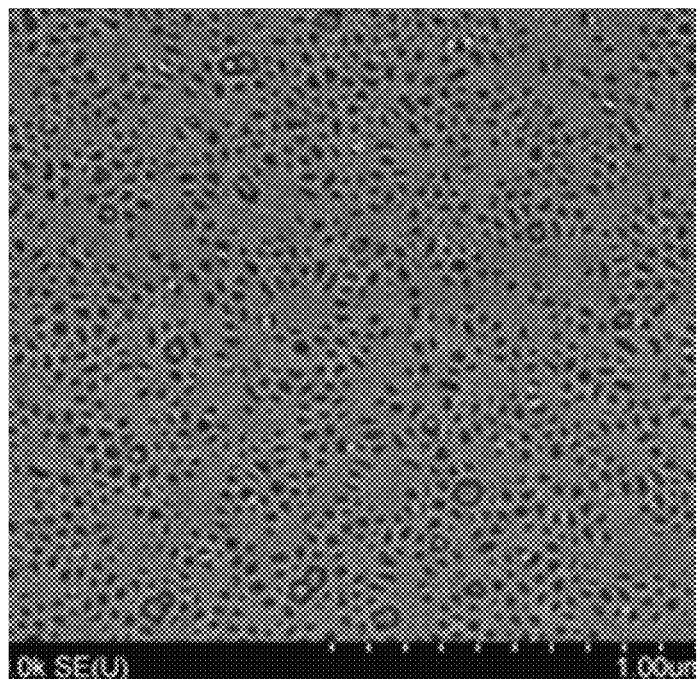
Figure 15:
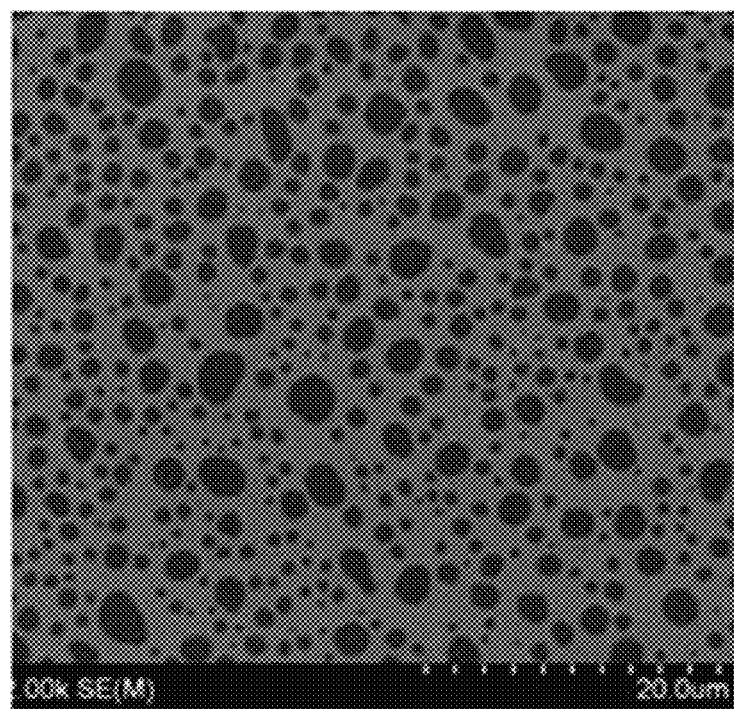

Self assembled polymer layers were prepared by using block copolymers of Examples 1 to 13 and Comparative Examples 1 and 2 and the results were observed. Specifically, each block copolymer was dissolved in solvent to a concentration of 1.0 weight % and then was spin-coated on a silicone wafer for 60 seconds by a speed of 3000 rpm. Then, self assembling was performed by a solvent annealing or a thermal annealing. The used solvents and aging methods were stated in the Table 1 below. Then, the self assembling properties were evaluated by subjecting each polymer layer to a SEM (scanning electron microscope) or AFM (atomic force microscopy) analysis. FIGS. 1 to 13 are results of Examples 1 to 13, respectively, and FIGS. 14 and 15 are results of Comparative Examples 1 and 2, respectively.

TABLE 1

| | The coating solution | | Annealing | |
|---|---|---|---|---|
| | The used solvent | The concentration of the block copolymer | Annealing method | Annealing condition |
| Ex. 1 | Toluene | 1.0 weight % | Thermal Annealing | 160° C., 1 hour |
| Ex. 2 | Toluene | 1.0 weight % | Thermal Annealing | 160° C., 1 hour |
| Ex. 3 | Toluene | 1.0 weight % | Thermal Annealing | 160° C., 1 hour |
| Ex. 4 | Toluene | 1.0 weight % | Thermal Annealing | 160° C., 1 hour |
| Ex. 5 | Toluene | 1.0 weight % | Thermal Annealing | 160° C., 1 hour |
| Ex. 6 | Toluene | 1.0 weight % | Solvent annealing | 2 hours |
| Ex. 7 | Dioxin | 1.0 weight % | Solvent annealing | 1 hours |
| Ex. 8 | Toluene | 1.0 weight % | Solvent annealing | 2 hours |
| Ex. 9 | Toluene | 1.0 weight % | Thermal Annealing | 160° C., 1 hour |
| Ex. 10 | Toluene | 1.0 weight % | Solvent annealing | 2 hours |
| Ex. 11 | Toluene | 1.0 weight % | Thermal Annealing | 160° C., 1 hour |
| Ex. 12 | Toluene | 1.0 weight % | Thermal Annealing | 200° C., 1 hour |

TABLE 1-continued

| | The coating solution | | Annealing | |
|---|---|---|---|---|
| | The used solvent | The concentration of the block copolymer | Annealing method | Annealing condition |
| Ex. 13 | Toluene | 1.0 weight % | Thermal Annealing | 160° C., 1 hour |
| Com. Ex. 1 | Toluene | 1.0 weight % | Thermal Annealing | 160° C., 1 hour |
| Com. Ex. 2 | Toluene | 1.0 weight % | Thermal Annealing | 160° C., 1 hour |

The solvent used in the solvent annealing of Example 6: the mixed solvent of THF (Tetrahydrofuran) and water (THF:water = 4:6 (weight ratio))
The solvent used in the solvent annealing of Example 7: chloroform
The solvent used in the solvent annealing of Example 8: the mixed solvent of THF (Tetrahydrofuran) and water (THF:water = 4:6 (weight ratio))
The solvent used in the solvent annealing of Example 10: cyclohexane Test Example 2

Figure 16:
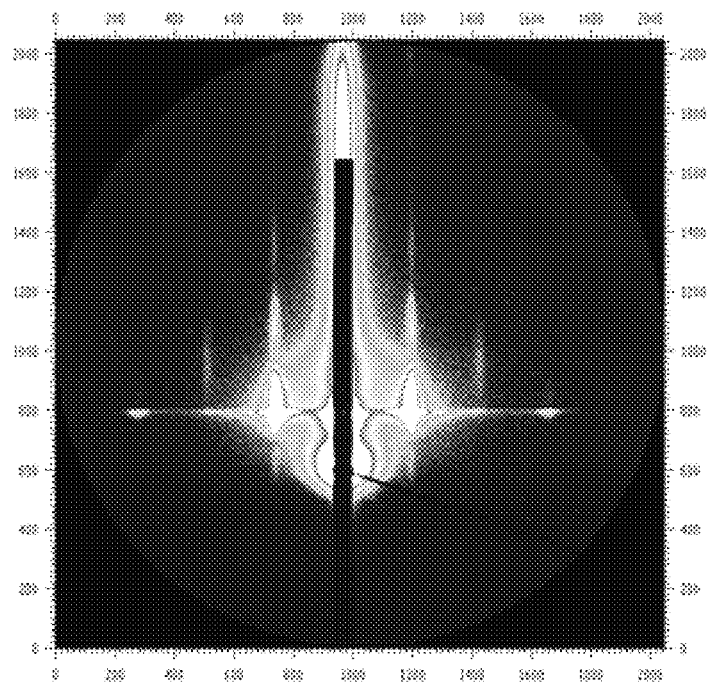
FIGS. 16 to 20 show results of the GISAXS to the polymer layers.
Figure 17:
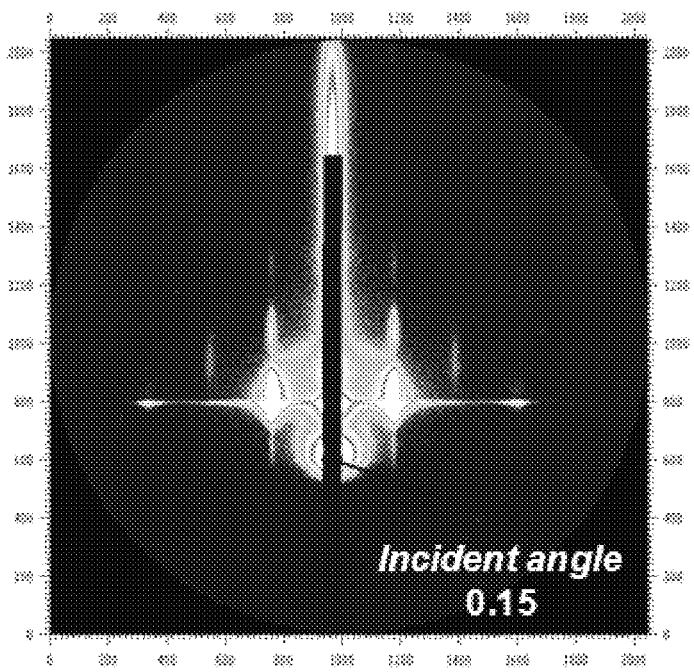

From the Test Example 1, it can be confirmed that the block copolymers in Examples have excellent self assembling properties fundamentally. Among Examples, GISAXS (Grazing Incident Small Angle X ray Scattering) properties were evaluated with respect to the block copolymer prepared in Example 1. The above property was evaluated in a 3C beam line of the Pohang Light Source. The polymer layer was formed by spin-coating a coating solution, which was prepared by dissolving the block copolymer of Example 1 in fluorobenzene so as for a solid content to be 0.7 weight %, on a substrate having a hydrophilic or hydrophobic surface so as for the coated layer to have a thickness of 5 nm (coated area: width=1.5 cm, length=1.5 cm) and drying it for about 1 hour at the room temperature and then subjecting it to the thermal annealing at about 160° C. for about 1 hour. The formed polymer layer was irradiated with X ray so as for an incident angle to be from about 0.12 degrees to 0.23 degrees, which corresponded to an angle between a critical angle of the layer and a critical angle of the substrate, and then the X ray diffraction pattern scattered from the layer was obtained by using a 2D marCCD. At this time, a distance from the layer to the detector was selected so as for the self assembled pattern in the layer to be effectively observed within a range from about 2 m to 3 m. As the substrate having the hydrophilic surface, the substrate having a wetting angle of about 5 degrees with respect to purified water at the room temperature was used, and, as the substrate having the hydrophobic surface, the substrate having a wetting angle of about 60 degrees with respect to purified water at the room temperature was used. FIG. 16 is the result of the GISAXS (Grazing Incident Small Angle X ray Scattering) analysis with respect to the surface having the wetting angle of about 5 degrees with respect to purified water at the room temperature according to the above method. FIG. 17 is the result of the GISAXS (Grazing Incident Small Angle X ray Scattering) analysis with respect to the surface, as the hydrophobic surface, having the wetting angle of about 60 degrees with respect to purified water at the room temperature according to the above method. From the Figures, it can be confirmed that the in-plane phase diffraction patterns are confirmed in any case, and the block copolymer of Example 1 has the vertical aligning property.

Further, block copolymers having different volume fractions were prepared according to the same method as in Example 1, except that the molar ratios of the monomers and the macroinitiators were controlled.

The volume fractions are as below.

TABLE 2

| | Volume fraction of the first block | Volume fraction of the second block |
|---|---|---|
| Sample 1 | 0.7 | 0.3 |
| Sample 2 | 0.59 | 0.41 |
| Sample 3 | 0.48 | 0.52 |

Figure 18:
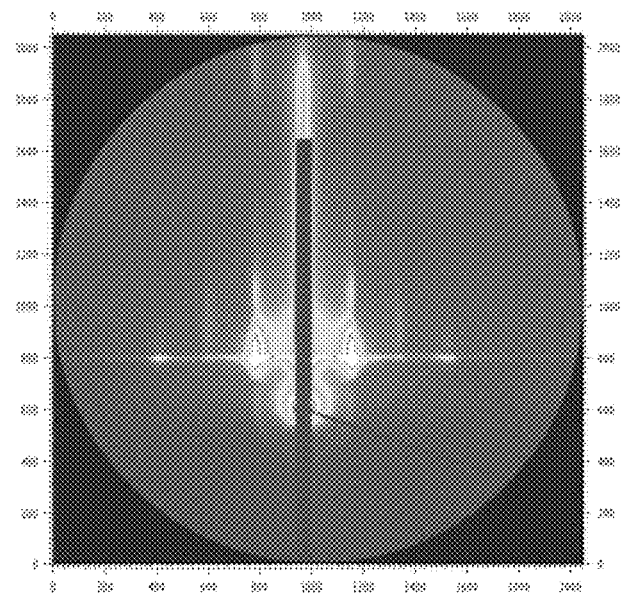
Figure 19:
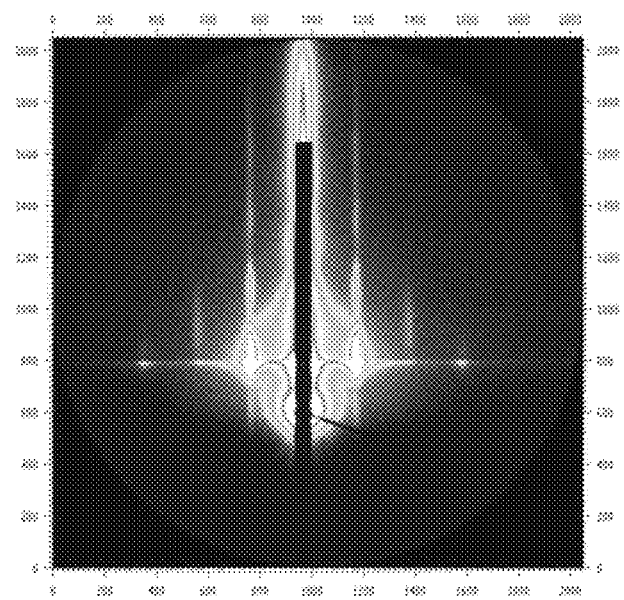
Figure 20:
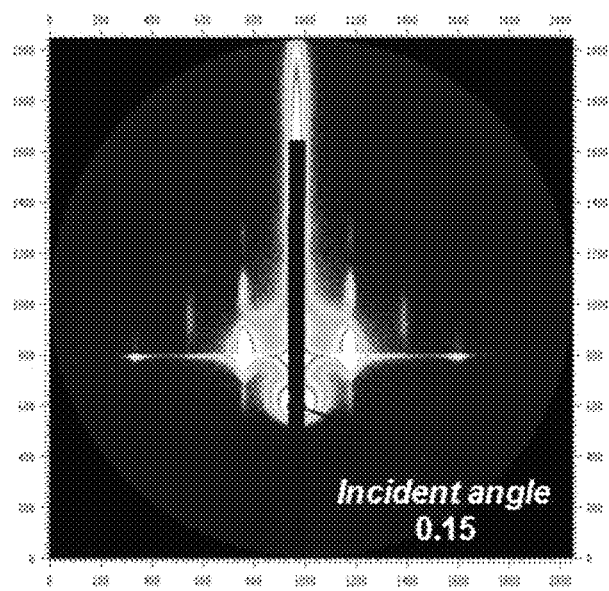

The volume fraction of each block of the block copolymer was calculated based on a molecular weight measured by a GPC (Gel Permeation Chromatogrph) and the density at the room temperature. In the above, the density was measured by the buoyancy method, specifically, was calculated by a mass in solvent (ethanol), of which a mass and a density in the air are known, and the GPC was performed according to the above described method. The results of the GISAXS analysis with respect to the each sample are illustrated in FIGS. 18 to 20. FIGS. 18 to 20 are results with respect to the samples 1 to 3, respectively, and from the figures, it can be confirmed that the in-plane phase diffraction patterns on GISAXS are observed, and therefrom it can be predicted to have the vertical aligning property.

Test Example 3

From the Test Example 1, it can be confirmed that the block copolymers in Examples have excellent self assembling properties fundamentally. Among Examples, surface energies and densities were evaluated with respect to Comparative Examples 1 and Examples 1 to 5 and 13, in which appropriate results were observed.

The surface energy was measured by using the drop shape analyzer (DSA 100 product from KRUSS, Co.). The surface energy was evaluated with respect to the polymer layer formed by spin-coating a coating solution, which was prepared by dissolving the material to be evaluated in fluorobenzene so as for a solid content to be 2 weight %, on a silicone wafer so as for the coated layer to have a thickness of 50 nm (coated area: width=2 cm, length=2 cm) and drying it for about 1 hour at the room temperature and then subjecting it to the thermal annealing at about 160° C. for about 1 hour. The surface energy was calculated from average values which were calculated from average values measured by dropping deionized water ($H_2O$) and diiodomethane, both of which are liquids of which surface tensions are known, 5 times respectively. In the below Table, the surface energy of each block is the surface energy measured with respect to a homopolymer formed by monomers forming the corresponding block according to the above method.

The method for measuring the density was the same as described above.

The measured results are stated in the below Table.

TABLE 3

| | | Exs. | | | | | | Com. Ex. |
|---|---|---|---|---|---|---|---|---|
| | | 1 | 2 | 3 | 4 | 5 | 13 | 1 |
| The first | SE | 30.83 | 31.46 | 27.38 | 26.924 | 27.79 | 37.37 | 48.95 |
| | De | 1 | 1.04 | 1.02 | 0.99 | 1.00 | 1.11 | 1.19 |

TABLE 3-continued

|  |  | Exs. | | | | | | Com. Ex. |
|---|---|---|---|---|---|---|---|---|
|  |  | 1 | 2 | 3 | 4 | 5 | 13 | 1 |
| Block | VF | 0.66 | 0.57 | 0.60 | 0.61 | 0.61 | 0.73 | 0.69 |
| The | SE | 24.4 | 24.4 | 24.4 | 24.4 | 24.4 | 24.4 | 24.4 |
| Second | De | 1.57 | 1.57 | 1.57 | 1.57 | 1.57 | 1.57 | 1.57 |
| Block | VF | 0.34 | 0.43 | 0.40 | 0.39 | 0.39 | 0.27 | 0.31 |
| Difference of SE | | 6.43 | 7.06 | 2.98 | 2.524 | 3.39 | 12.98 | 24.55 |
| Difference of De | | 0.57 | 0.53 | 0.55 | 0.58 | 0.57 | 0.46 | 0.38 |

SE: surface energy (unit: mN/m)
De: density (unit: g/cm$^3$)
VF: volume fraction
Difference of SE: the absolute value of the difference between the surface energies of the first and the second block
Difference of De: the absolute value of the difference between the densities of the first and the second block
Chain-forming atoms: the number of the chain-forming atoms in the first block
Interval: interval (unit: nm) between the first blocks in the self assembled block copolymer
n/D: the number of the chain-forming atoms in the first block/Interval between the first blocks in the self assembled block copolymer
Ref.: Polystyrene-polymethylmethacrylate block copolymer (the first block: polystyrene block, the second block: polymethylmethacrylate block)

From the above table, it can be confirmed that there are specific tendencies in the cases (Examples 1 to 5) where the appropriate self assembling properties are confirmed. Specifically, in the block copolymers of Examples 1 to 5, the absolute values of differences between surface energies of the first and second blocks are within a range from 2.5 mN/m to 7 mN/m; however Example 13 and Comparative Example 1 show the absolute values of difference between the surface energies that do not fall within the above range. Further, the first block shows a higher surface energy than the second block, and the range are from 20 mN/m to 35 mN/m. Further, the absolute values of differences between densities of the first and second blocks of the block copolymers of Examples 1 to 5 are 0.3 g/cm$^3$ or more.

Test Example 4

The result of the XRD analysis with respect to Comparative Example 1 and Examples 1 to 5 and 13, in which appropriate results were observed, is illustrated in the below Table 4.

TABLE 4

|  | Exs. | | | | | | Com. Ex. |
|---|---|---|---|---|---|---|---|
|  | 1 | 2 | 3 | 4 | 5 | 13 | 2 |
| Scattering vector (the q value) (unit: nm$^{-1}$) | 1.96 | 2.41 | 2.15 | 1.83 | 1.72 | 4.42 | 3.18 |
| FWHM (unit: nm$^{-1}$) | 0.57 | 0.72 | 0.63 | 0.45 | 0.53 | 0.97 | 1.06 |

The XRD pattern was evaluated by measuring the scattering intensity according to the scattering vector (q) by passing X ray through a sample in a 3C beam line of the Pohang Light Source. As the sample, powder obtained from the block copolymer to which any specific pre-treatment was not performed by purifying it so as to remove impurities therefrom was used after putting it in a cell for measurement of the XRD. During the XRD pattern analysis, as the X ray, X ray, a vertical size of which is 0.023 mm and a horizontal size of which is 0.3 mm was used and, as the detector, the measuring device (for example, 2D marCCD) was used. A 2D diffraction pattern scattered from the sample was obtained as an image, the obtained diffraction pattern was calibrated to the scattering vector (q) by using a silver behenate and then is circular averaged and then plotted as the scattering intensity according to the scattering vector (q). The position and the FWHM of the peak was obtained by plotting the scattering intensity according to the scattering vector (q) and peak fitting. From the above result, it can be confirmed the block copolymers showing excellent self assembling properties show specific XRD patterns, compared to Comparative Examples in which self assembling properties were not confirmed. Specifically, peaks of which the FWHMs is within a range from 0.2 nm$^{-1}$ to 1.5 nm$^{-1}$ are observed within a scattering vector's range from 0.5 nm$^{-1}$ to 10 nm$^{-1}$; however such peaks are not observed in Example 13 and Comparative Example 1.

What is claimed is:

1. A block copolymer comprising a block represented by the Formula 4 below and exhibiting an X ray diffraction peak, the peak having a full width at half maximum ranging from 0.2 nm$^{-1}$ to 1.5 nm$^{-1}$, within a q value range from 0.5 nm$^{-1}$ to 10 nm$^{-1}$:

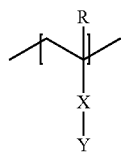

[Formula 4]

wherein the R is hydrogen or an alkyl group, the X is an oxygen atom, a sulfur atom, —S(=O)$_2$—, a carbonyl group, an alkenylene group, an alkynylene group, C(=O)—X$_1$— or —X$_1$—C(=O)—, where the X$_1$ is an oxygen atom, a sulfur atom, —S(=O)$_2$—, an alkylene group, an alkenylene group or an alkynylene group and the Y is a monovalent substituent comprising an aromatic structure to which a linear chain having at least 3 chain-forming atoms is linked.

2. The block copolymer according to claim 1, wherein the R is hydrogen or an alkyl group having 1 to 4 carbon atom(s).

3. The block copolymer according to claim 1, wherein the X is an oxygen atom, —C(=O)—O— or —O—C(=O)—.

4. The block copolymer according to claim 1, wherein the X is —C(=O)—O—.

5. The block copolymer according to claim 1, wherein the chain linked to the aromatic structure comprises 8 to 20 chain-forming atoms.

6. The block copolymer according to claim 1, wherein the chain-forming atom is carbon, oxygen or nitrogen.

7. The block copolymer according to claim 1, wherein the chain is a hydrocarbon chain.

8. The block copolymer according to claim 1, wherein the chain is directly linked to the aromatic structure or the chain is linked to the aromatic structure via a linker.

9. The block copolymer according to claim 8, wherein the linker is an oxygen atom, a sulfur atom, —NR$_3$—, —S(=O)$_2$—, an alkylene group, an alkenylene group or an alkynylene group, where the R$_3$ is hydrogen, an alkyl group, an alkenyl group, an alkynyl group, an alkoxy group or an aryl group.

10. The block copolymer according to claim 1, wherein the aromatic structure comprises 6 to 12 carbon atoms.

11. The block copolymer according to claim 1, the Y is represented by Formula 2 below:

—P-Q-Z

[Formula 2]

wherein the P is an arylene group, the Q is a single bond, an oxygen atom or —NR$_3$—, where the R$_3$ is hydrogen, an alkyl group, an alkenyl group, an alkynyl group, an alkoxy group or an aryl group and the Z is the chain having 3 or more chain-forming atoms.

12. The block copolymer according to claim 1, wherein a ratio (n/D) of the number (n) of the chain-forming atoms of the chain relative to the distance (D, unit: nm) between the blocks in a self assembled state is from 2.5 nm$^{-1}$ to 5 nm$^{-1}$.

13. The block copolymer according to claim 1, wherein a volume fraction of the block represented by the Formula 4 is in a range from 0.4 to 0.8.

14. The block copolymer according to claim 1, further comprising a second block, an absolute value of a difference between surface energies of the block represented by the Formula 4 and the second block being in a range from 2.5 mN/m to 7 mN/m.

15. The block copolymer according to claim 14, wherein the block represented by the Formula 4 has a higher surface energy than the second block.

16. The block copolymer according to claim 1, wherein the surface energy of the block represented by the Formula 4 is in a range from 20 mN/m to 35 mN/m.

17. The block copolymer according to claim 1, further comprising a second block, an absolute value of a difference between densities of the block represented by the Formula 4 and the second block being 0.3 g/cm$^3$ or more.

18. A polymer layer comprising a self assembled product of the block copolymer of claim 1.

19. A method for forming a polymer layer, comprising forming the polymer layer comprising a self assembled product of the block copolymer of claim 1.

20. A pattern-forming method comprising selectively removing the block represented by the Formula 4 or a block different from the block represented by the Formula 4 of the block copolymer from a laminate comprising a substrate and a polymer layer that is formed on the substrate and that comprises a self-assembled product of the block copolymer of claim 1.

21. A block copolymer comprising a block represented by the Formula 4 below and exhibiting an X ray diffraction peak, the peak having a full width at half maximum ranging from 0.2 nm$^{-1}$ to 1.5 nm$^{-1}$, within a q value range from 0.5 nm$^{-1}$ to 10 nm$^{-1}$:

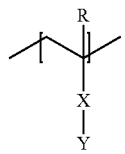

[Formula 4]

wherein the R is hydrogen or an alkyl group, the X is an oxygen atom, a sulfur atom, —S(=O)$_2$—, a carbonyl group, an alkylene group, an alkenylene group, an alkynylene group, —C(=O)—X$_1$— or —X$_1$—C(=O)—, where the X$_1$ is an oxygen atom, a sulfur atom, —S(=O)$_2$—, an alkylene group, an alkenylene group or an alkynylene group and the Y is a monovalent substituent comprising an aromatic structure to which a linear chain having at least 3 chain-forming atoms is linked, wherein the chain is linked to the aromatic structure via a linker, and wherein the linker is an oxygen atom, a sulfur atom, —NR$_3$—, —S(=O)$_2$—, an alkenylene group or an alkynylene group, where the R$_3$ is hydrogen, an alkyl group, an alkenyl group, an alkynyl group, an alkoxy group or an aryl group.

* * * * *